US007790868B2

(12) United States Patent
Campbell et al.

(10) Patent No.: US 7,790,868 B2
(45) Date of Patent: Sep. 7, 2010

(54) TEAL FLUORESCENT PROTEINS (MTFP1)

(75) Inventors: Robert Earl Campbell, Edmonton (CA); Hui-Wang Ai, Edmonton (CA)

(73) Assignee: The Governors of the University of Alberta, Edmonton, Alberta (CA)

( * ) Notice: Subject to any disclaimer, the term of this patent is extended or adjusted under 35 U.S.C. 154(b) by 0 days.

(21) Appl. No.: 11/419,437

(22) Filed: May 19, 2006

(65) Prior Publication Data
US 2006/0275827 A1 Dec. 7, 2006

Related U.S. Application Data

(60) Provisional application No. 60/682,848, filed on May 20, 2005.

(51) Int. Cl.
| C07H 21/04 | (2006.01) |
| C12N 15/63 | (2006.01) |
| C12N 15/85 | (2006.01) |
| C12N 15/86 | (2006.01) |
| C12N 1/20 | (2006.01) |
| C12N 1/21 | (2006.01) |
| C12N 1/15 | (2006.01) |
| C12N 5/14 | (2006.01) |
| C12N 1/19 | (2006.01) |

(52) U.S. Cl. .................... 536/23.1; 435/320.1; 435/325; 435/252.1; 435/252.3; 435/254.11; 435/419; 435/254.2

(58) Field of Classification Search ........................ None
See application file for complete search history.

(56) References Cited

U.S. PATENT DOCUMENTS

| 6,020,192 A * | 2/2000 | Muzyczka et al. ....... 435/320.1 |
| 6,969,597 B2 | 11/2005 | Lukyanov et al. |
| 2003/0059835 A1 | 3/2003 | Tsien et al. |

FOREIGN PATENT DOCUMENTS

WO 01/27150 4/2001

OTHER PUBLICATIONS

Ngo et al., in The Protein Folding Problem and Tertiary Structure Prediction, 1994, Merz et al. (ed.), Birkhauser, Boston, MA, pp. 433 and 492-495.*
Blast 2 Sequences, sequence alignment results. Retrieved from the Internet <URL:http://www.ncbi.nlm.nih.gov/blast/bl2seq/wblast2.cgi>.*
James, Douglas R., et al. "Stoboscopic Optical Boxcar Technique for the Determination of Fluorescence Lifetimes", Review of Scientific Instruments 63, pp. 1710-1716 (1992).
Matz, Mikhail V., et al. "Fluorescent Proteins from Nonbioluminescent Anthozoa Species", Nat. Biotechnol 17, pp. 969-973 (1999).
Miyawaki, A., et al. "Monitoring Protein Conformations and Interactions by Fluorescence Resonance Energy Transfer between Mutants of Green Fluorescent Protein", Methods Enzymol., 327, pp. 472-500 (2000).
Nguyen, Annalee W., et al., "Evolutionary Optimization of Fluorescent Proteins fro Intracellular FRET", Nat. Biotechnol 23, pp. 355-360 (2005).
Ormo, Mats, et al. "Crystal Structure of the *Aequorea victoria* Green Fluorescent Protein", Science 273, pp. 1392-1395 (1996).
Shimomura, O. "Structure of the Chromophore of *Aequorea* Green Fluorescent Protein", Febs. Letters 104. pp. 220-222 (1979).
Sun, Yi, et al. "Biophysical Characterization of Natural and Mutant Fluorescent Protein Cloned from Zooxanthellate Corals", FEBS Lett., 570:175-83, (2004).
Tsien, Roger Y., "The Green Fluorescent Protein", Annul Rev. Biochem., 67:509-44 (1998).
Ward, William W., "Biochemical and Physical Properties of Green Fluorescent Protein", Properties, Applications and Protocols (ed. M.K. Chalfie, S.) 45-75 (Wiley, New York; 1998).
Yang, Fan, et al. "The Molecular Structure of Green Fluorescent Protein", Nat. Biotechnol 14, pp. 1246-1251 (1996).
Brannon, James H., et al. "Absolute Quantum Yield Determination by Thermal Blooming", Journal of Physical Chemistry 82, pp. 705-709 (1978).
Fromant, Michel, et al. "Direct Random Mutagenesis of Gene-Sized DNA Fragments Using Polymerase Chain Reaction", Anal. Biochem. 224, pp. 347-353 (1995).
Heim, Roger, et al. "Wavelength Mutations and Posttranslations autoxidation of green fluorescent protein", Proc. Nat. Acad. Sci. U.S.A. 91: pp. 12501-12504, (1994).
Heim, Roger, et al. "Improved Green Fluorescence", Nature vol. 373, pp. 663-664 (1995).

* cited by examiner

*Primary Examiner*—David J Steadman
*Assistant Examiner*—Jae W Lee
(74) *Attorney, Agent, or Firm*—Bennett Jones LLP

(57) ABSTRACT

The present invention provides an isolated nucleic acid sequence encoding a non-oligomerizing *Clavularia* teal fluorescent protein (mTFP) variant having a tyrosine-derived chromophore, as well as fragments and derivatives thereof. Also provided is a method for engineering the nucleic acid sequence, a vector comprising the nucleic acid sequence, a host cell comprising the vector, and use of the vector in a method for expressing the nucleic acid sequence. The present invention further provides an isolated nucleic acid, or mimetic or complement thereof, that hybridizes under stringent conditions to the nucleic acid sequence. Additionally, the present invention provides a non-oligomerizing mTFP variant encoded by the nucleic acid sequence, as well as derivatives, fragments, and homologues thereof. Also provided is an antibody that specifically binds to the mTFP variant. The present invention further provides a tandem dimer comprising two mTFP dimers, operatively linked by a peptide linker.

10 Claims, 22 Drawing Sheets

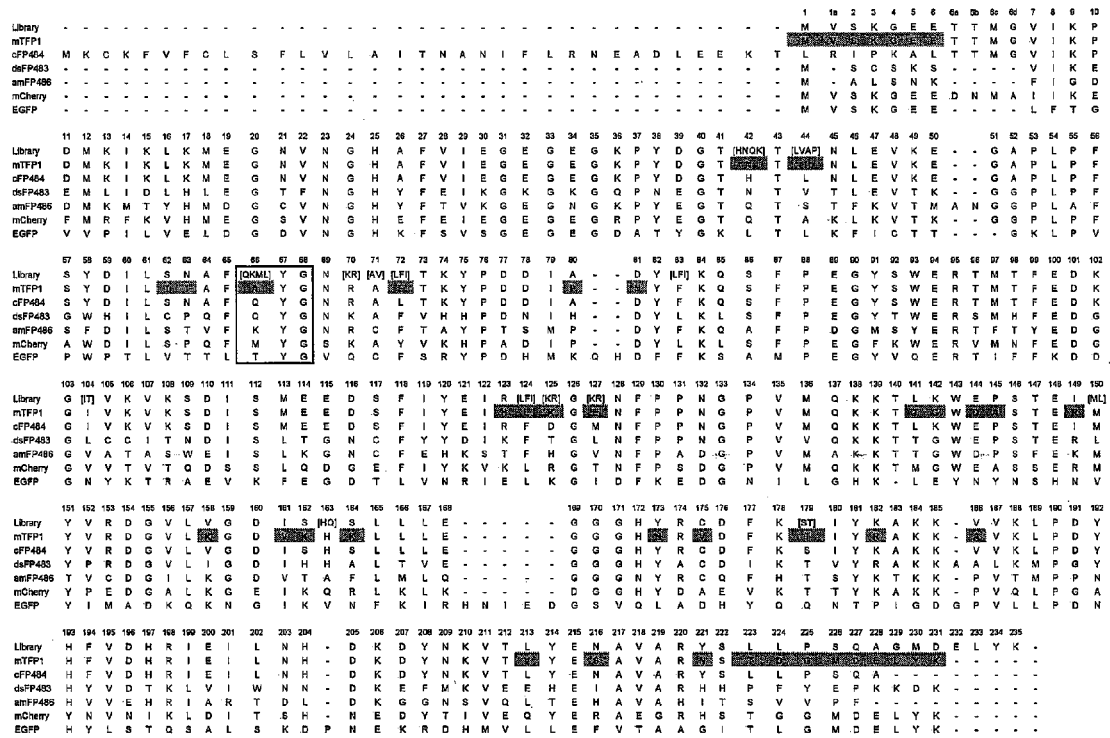
Figure 3: Protein sequence alignments of mTFP1, coral CFPs, and relevant homologues.

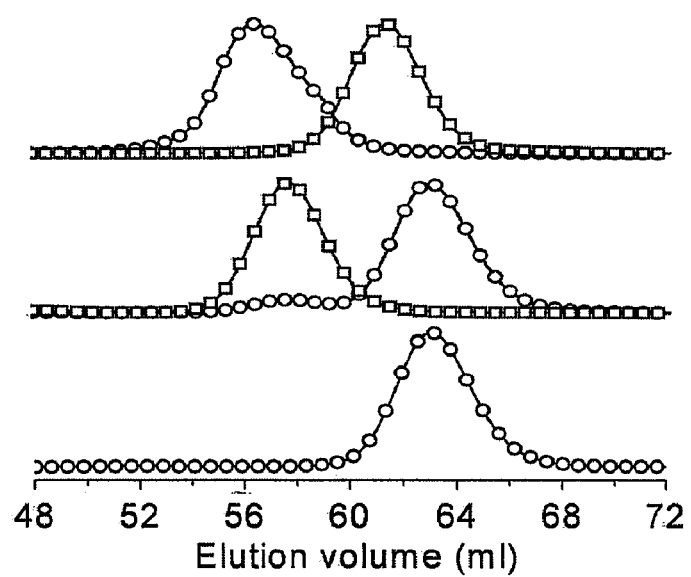
Figure 4: Characterization of mTFP1 by Gel Filtration Chromatography.

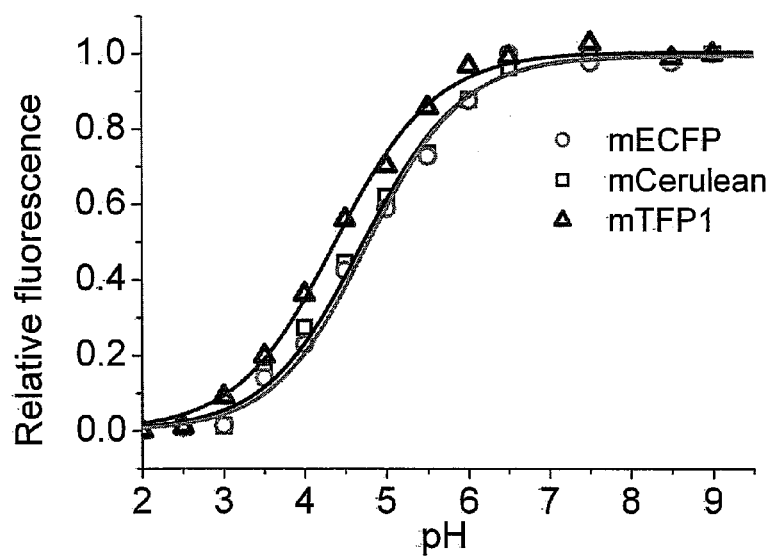
Figure 5: pH-Dependence of the fluorescence emission of mECFP, mCerulean, and mTFP1.

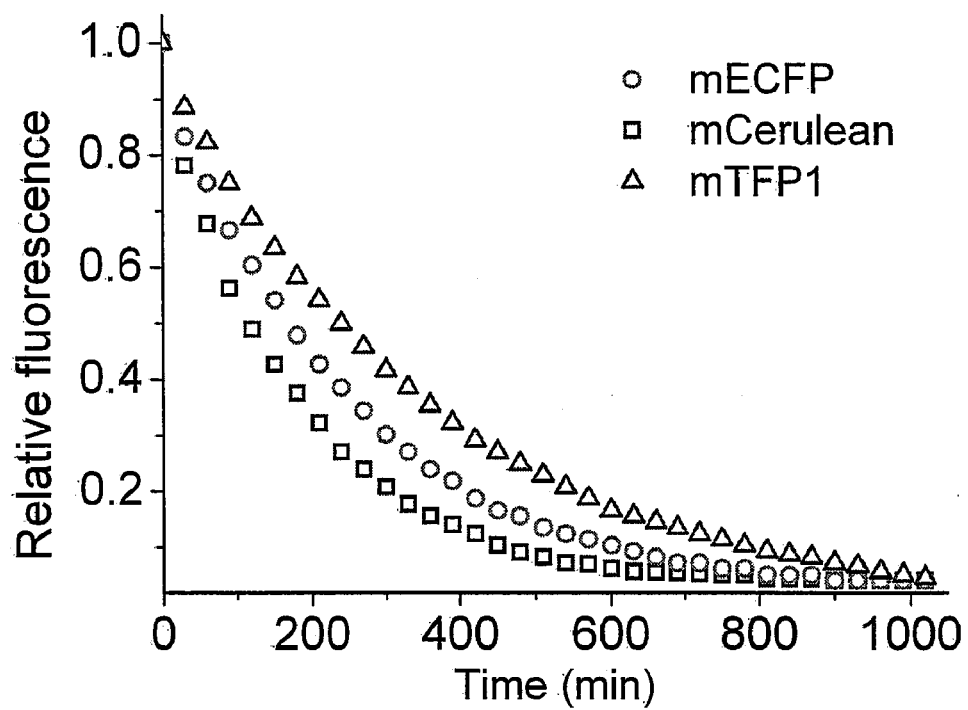
Figure 6: Relative rates of photobleaching of mECFP, mCerulean, and mTFP1.

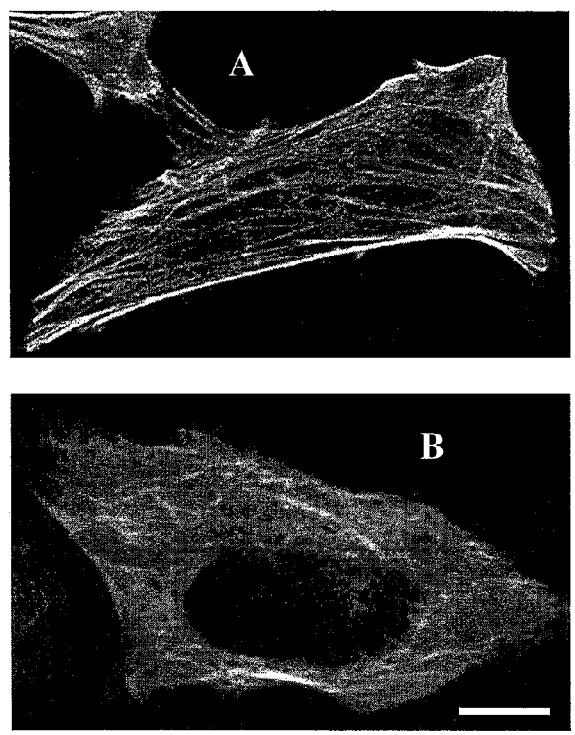
Figure 7: Confocal fluorescence image of a Hela cell expressing mTFP1-actin (scale bar = 10 μm).

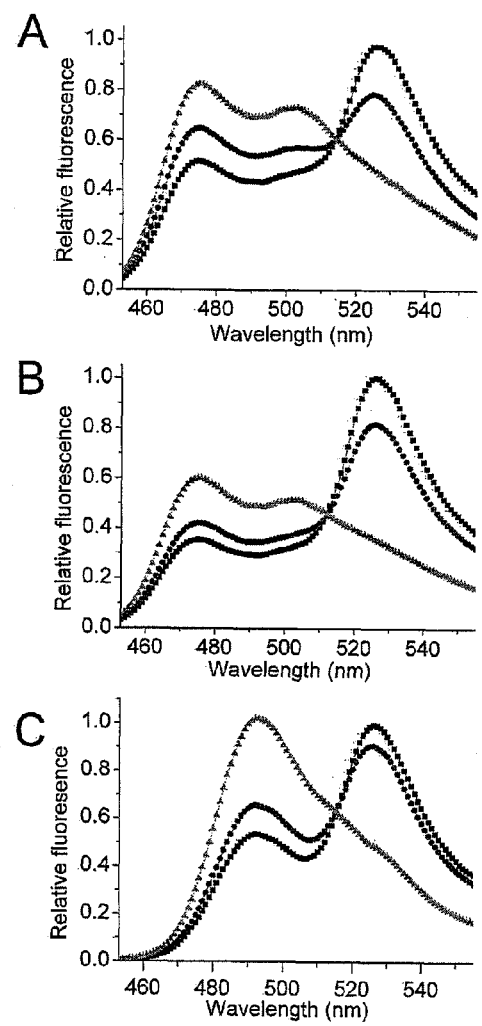
Figure 8: *In vitro* FRET responses for Cameleon constructs containing (A) mECFP, (B) mCerulean, and (C) mTFP1.

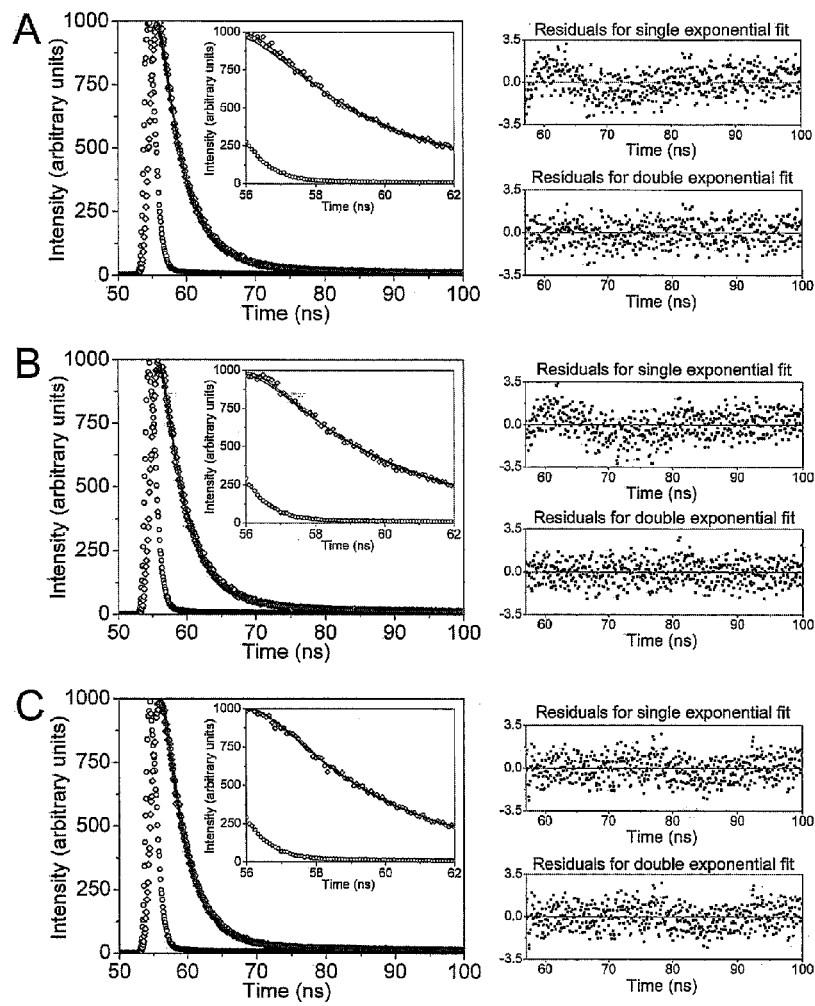
Figure 9: Fluorescence lifetime decay data for (A) mECFP, (B) mCerulean, and (C) mTFP1.

FIG. 10A

SEQ ID NO: 2 (mTFP0.86)

atggtgagcaagggcgaggagaccacaatgggcgtaatcaagcccgacatgaagatcaag
ctgaagatggagggcaacgtgaatggccacgccttcgtgatcgagggcgagggcgagggc
aagccctacgacggcaccaacaccatcaacctggaggtgaaggagggagccccccctgccc
ttctcctacgacattctgaccaacgccttcgcttacggcaacagggccttcaccaagtac
cccgacgacatccccaactacttcaagcagtccttccccgagggctactcttgggagcgc
accatgaccttcgaggacaagggcatcgtgaaggtgaagtccgacatctccatggaggag
gactccttcatctacgagatacgcctcaagggcgagaacttccccccccaacggccccgtg
atgcagaagaagaccctgaagtgggagccctccaccgagatcctgtacgtgcgcgacggc
gtgctggtgggcgacatcaagcacaagctgctgctggagggcggcggccactaccgcgtt
gacttcaagaccatctacagggccaagaaggcggtgaagctgcccgactaccacttcgtg
gaccaccgcatcgagatcctgaaccacgacaaggactacaacaaggtgaccgtttacgag
agcgccgtggcccgctactccaccggcggcatggacgagctgtacaag

FIG. 10B

SEQ ID NO: 6 (mTFP1)

atggtgagcaagggcgaggagaccacaatgggcgtaatcaagcccgacatgaagatcaag
ctgaagatggagggcaacgtgaatggccacgccttcgtgatcgagggcgagggcgagggc
aagccctacgacggcaccaacaccatcaacctggaggtgaaggagggagccccccctgccc
ttctcctacgacattctgaccaccgcgttcgcctacggcaacagggccttcaccaagtac
cccgacgacatccccaactacttcaagcagtccttccccgagggctactcttgggagcgc
accatgaccttcgaggacaagggcatcgtgaaggtgaagtccgacatctccatggaggag
gactccttcatctacgagatacacctcaagggcgagaacttccccccccaacggccccgtg
atgcagaagaagaccaccggctgggacgcctccaccgagaggatgtacgtgcgcgacggc
gtgctgaagggcgacgtcaagcacaagctgctgctggagggcggcggccaccaccgcgtt
gacttcaagaccatctacagggccaagaaggcggtgaagctgcccgactatcactttgtg
gaccaccgcatcgagatcctgaaccacgacaaggactacaacaaggtgaccgtttacgag
agcgccgtggcccgcaactccaccgacggcatggacgagctgtacaagtaa

Fig. 10

SEQ ID NO: 3 (mTFP0.86)

AGCAGGTCTAGACTCGAGCATGGTGAGCAAGGGCGAGGAGACCACAATGGGCGTA
ATCAAGCCCGACATGAAGATCAAGCTGAAGATGGAGGGCAACGTGAACGGCCACG
CCTTCGTGATCGAGGGCGAGGGCGAGGGCAAGCCCTACGACGGCACCMASACCSYC
AACCTGGAGGTGAAGGAGGGAGCCCCCCTGCCCTTCTCCTACGACATCCTGTCCAAC
GCCTTCMWGTACGGCAACARGGYCHTCACCAAGTACCCCGACGACATCGCCGACTA
CHTCAAGCAGTCCTTCCCCGAGGGCTACTCCTGGGAGCGCACCATGACCTTCGAGGA
CAAGGGCAYCGTGAAGGTGAAGTCCGACATCTCCATGGAGGAGGACTCCTTCATCT
ACGAGATCCGCHTCARGGGCARGAACTTCCCCCCCAACGGCCCCGTGATGCAGAAG
AAGACCCTGAAGTGGGAGCCCTCCACCGAGATCMTGTACGTGCGCGACGGCGTGCT
GGTGGGCGACATCTCCCASTCCCTGCTGCTGGAGGGCGGCGGCCACTACCGCTGCGA
CTTCAAGWCCATCTACAAGGCCAAGAAGGTGGTGAAGCTGCCCGACTACCACTTCG
TGGACCACCGCATCGAGATCCTGAACCACGACAAGGACTACAACAAGGTGACCCTG
TACGAGAACGCCGTGGCCCGCTACTCCCTGCTGCCCTCCCAGGCAGGCATGGACGA
GCTGTACAAGTAAGAATTCGGATCCTGCGTA

SEQ ID NO: 3 (mTFP0.86)

MVSKGEETTMGVIKPDMKIKLKMEGNVNGHAFVIEGEGEGKPYDGTNTINLEVKEGAP
LPFSYDILTNAFAYGNRAFTKYPDDIPNYFKQSFPEGYSWERTMTFEDKGIVKVKSDISM
EEDSFIYEIRLKGENFPPNGPVMQKKTLKWEPSTEILYVRDGVLVGDIKHKLLLEGGGHY
RVDFKTIYRAKKAVKLPDYHFVDHRIEILNHDKDYNKVTVYESAVARYSTGGMDELYK

FIG. 12B

SEQ ID NO: 7 (mTFP1)

MVSKGEETTMGVIKPDMKIKLKMEGNVNGHAFVIEGEGEGKPYDGTNTINLEVKEGAP
LPFSYDILTTAFAYGNRAFTKYPDDIPNYFKQSFPEGYSWERTMTFEDKGIVKVKSDISM
EEDSFIYEIHLKGENFPPNGPVMQKKTTGWDASTERMYVRDGVLKGDVKHKLLLEGGG
HHRVDFKTIYRAKKAVKLPDYHFVDHRIEILNHDKDYNKVTVYESAVARNSTDGMDEL
YK

Fig. 12

SEQ ID NO: 4 (tdTFP0.3)

atggtgagcaagggcgaggagaccacaatgggcgtaatcaagcccgacatgaagatcaagctgaagatggagggcaacgtgaatggcc
acgccttcgtgatcgagggcgagggcgagggcaagccctacgacggcaccaacaccgtcaacctggaggtgaaggagggagccccc
ctgcccttctcctacgacattctgtccaacgccttcgggtacggcaacagggccttcaccaagtaccccgacgacatcgccaactacttcaa
gcagtccttccccgagggctactcctgggagcgcaccatgaccttcgaggacaagggcatcgtgaaggtgaagtccgacatctccatgga
ggaggactccttcatctacgagatccgcctcaagggcaagaacttcccccccaacggccccgtgatgcagaagaagaccctgaagtggg
agccctccaccgagatcctgtacgtgcgcgacggcgtgctggtgggcgacatctcccactccctgctgctggagggcggcggccactac
cgctgcgacttcaagaccatctacagggccaagaaggtggtgaagctgcccgactaccacttcgtggaccaccgcatcgagatcctgaac
cacgacaaggactacaacaaggtgaccctgtacgagaacgccgtggcccgctactccctgctgcccctcccaggcaaccggcagcactct
agtcagcggctccggcaccgccaccacaatgggcgtaatcaagcccgacatgaagatcaagctgaagatggagggcaacgtgaatggc
cacgccttcgtgatcgagggcgagggcgagggcaagccctacgacggcaccaacaccgtcaacctggaggtgaaggagggagcccc
cctgcccttctcctacgacattctgtccaacgccttcgggtacggcaacagggccttcaccaagtaccccgacgacatcgccaactacttca
agcagtccttccccgagggctactcctgggagcgcaccatgaccttcgaggacaagggcatcgtgaaggtgaagtccgacatctccatgg
aggaggactccttcatctacgagatccgcctcaagggcaagaacttcccccccaacggccccgtgatgcagaagaagaccctgaagtgg
gagccctccaccgagatcctgtacgtgcgcgacggcgtgctggtgggcgacatctcccactccctgctgctggagggcggcggccacta
ccgctgcgacttcaagaccatctacagggccaagaaggtggtgaagctgcccgactaccacttcgtggaccaccgcatcgagatcctgaa
ccacgacaaggactacaacaaggtgaccctgtacgagaacgccgtggcccgctactccctgctgccccccaggcaggcatggacgag
ctgtacaag

Fig. 13

SEQ ID NO: 5 (tdTFP0.3)

MVSKGEETTMGVIKPDMKIKLKMEGNVNGHAFVIEGEGEGKPYDGTNTVNLEVKEGAP
LPFSYDILSNAFGYGNRAFTKYPDDIANYFKQSFPEGYSWERTMTFEDKGIVKVKSDISM
EEDSFIYEIRLKGKNFPPNGPVMQKKTLKWEPSTEILYVRDGVLVGDISHSLLLEGGGHY
RCDFKTIYRAKKVVKLPDYHFVDHRIEILNHDKDYNKVTLYENAVARYSLLPSQATGST
LVSGSGTATTMGVIKPDMKIKLKMEGNVNGHAFVIEGEGEGKPYDGTNTVNLEVKEGA
PLPFSYDILSNAFGYGNRAFTKYPDDIANYFKQSFPEGYSWERTMTFEDKGIVKVKSDIS
MEEDSFIYEIRLKGKNFPPNGPVMQKKTLKWEPSTEILYVRDGVLVGDISHSLLLEGGGH
YRCDFKTIYRAKKVVKLPDYHFVDHRIEILNHDKDYNKVTLYENAVARYSLLPPQAGM
DELYK

| Residue | Mutated to | Codon | Cumulative library size |
|---|---|---|---|
| Ile104 | I,T | AYC | $2^1 = 2$ |
| Asp125 | K,R | ARG | $2^2 = 4$ |
| Met127 | K,R | ARG | $2^3 = 8$ |
| His42 | H,N,Q,K | MAS | $2^3 * 4^1 = 32$ |
| Leu44 | L,V,A,P | SYC | $2^3 * 4^2 = 128$ |
| Gln66 | Q,K,M,L | MWG | $2^3 * 4^3 = 512$ |
| Arg70 | K,R | ARG | $2^4 * 4^3 = 1024$ |
| Val71 | A,V | GYC | $2^5 * 4^3 = 2048$ |
| Leu72 | L,F,I | HTC | $2^5 * 3^1 * 4^3 = 6144$ |
| Phe83 | L,F,I | HTC | $2^5 * 3^2 * 4^3 = 18432$ |
| Phe124 | L,F,I | HTC | $2^5 * 3^3 * 4^3 = 55296$ |
| Met150 | M,L | MTG | $2^6 * 3^3 * 4^3 = 110592$ |
| His163 | H,Q | CAS | $2^7 * 3^3 * 4^3 = 221184$ |
| Ser179 | S,T | WCC | $2^8 * 3^3 * 4^3 = 442368$ |

TEAL FLUORESCENT PROTEINS (MTFP1)

CROSS REFERENCE TO RELATED APPLICATIONS

The present application claims priority benefit of U.S. Provisional Patent Application No. 60/682,848 filed on May 20, 2005, the contents of which are incorporated herein by reference.

FIELD OF THE INVENTION

The present invention relates to fluorescent proteins and, in particular, monomeric teal fluorescent proteins.

BACKGROUND

The *Aequorea Victoria* green fluorescent protein (GFP), along with its various homologues and mutants (Shaner, 2005; Shimomura, 1979), has enabled live-cell fluorescence imaging of recombinant fusion proteins to become a popular and widely-accessible technique in cell-biology research (Tsien, 1998; Zhang, 2002). The defining feature of *Aequorea* GFP is its ability to autonomously generate a green fluorophore within the confines of its distinctive β-barrel structure (Shimomura, 1979; Yang, 1996; Ormo, 1996). The chromophore of GFP is post-translationally and autonomously generated, through a stepwise process that involves a main-chain cyclization (Gly67 N to Ser65 C), a dehydration (Ser65 C-N), and an oxidation (Tyr66 Ca-C) that effectively conjugates the phenolic side chain of tyrosine 66 to a five-membered ring heterocycle formed from the main-chain atoms of serine 65, tyrosine 66, and glycine 67 (FIG. 1). In the ground state of the wild-type GFP, the chromophore exists as a mixture of neutral phenol (maximum absorbance at 395 nm) and anionic phenolate forms (maximum absorbance at 475 nm). In the excited state, the neutral phenol form deprotonates to form the phenolic anion; therefore, only a single fluorescence emission peak (maximum fluorescence at 504 nm) is observed.

The steric, electrostatic, and hydrogen-bonding environment imposed upon the chromophore by the surrounding residues strongly influences the fluorescence properties. The GFP chromophore has proven remarkably amenable to genetic modification of both its covalent structure and its local environment, and this tolerance has been exploited for the creation of wavelength-shifted variants (Tsien, 1998). *Aequorea* GFP variants (Shaner, 2005) have been engineered with altered colors, brightness, photostability, ion-sensitivity (Hanson, 2002), and photoswitching properties (Lukyanov, 2005). Amino-acid substitutions at position 65 and at several other residues in the immediate vicinity of the chromophore (e.g., position 203) have resulted in GFP variants (i.e., enhanced GFP (EGFP) with maximum fluorescence at 510 nm. A particularly important class of useful variants that have resulted from such efforts are the yellow fluorescent proteins (YFPs) that are defined by the Thr203Tyr mutation (Ormo, 1996) and an emission peak that is ~25 nm red-shifted from the wild type emission peak of ~504-509 nm. However, at present, there is no known report of an *Aequorea* GFP mutant with a tyrosine-derived chromophore and fluorescence that is blue-shifted relative to the wild-type protein (i.e., it has a maximum fluorescence that is less than 504 nm).

The term "cyan fluorescent protein", or "CFP", is generally reserved for any GFP homologue with maximum fluorescence emission between approximately 470 nm and 495 nm. To date, substitutions of tyrosine 66 to other aromatic amino acids have proved to be the only approach for blue-shifting the fluorescence emission relative to the wild-type protein, in order to produce a CFP. For example, the widely used *Aequorea* GFP-derived CFP known as avCFP (also commonly known as ECFP or CFP) was engineered by replacing Tyr66 of *Aequorea* GFP with a tryptophan, to give an indole-containing chromophore (FIG. 1) (Heim, 1994) that had an emission peak in the cyan region (~480 nm) of the visible spectrum. Although the original Tyr66Trp mutant of *Aequorea* GFP was only weakly fluorescent, efforts to improve the brightness yielded the widely used variant ECFP (Heim, 1994; Miyawaki, 1997) and more recently-Cerulean (Rizzo, 2004) and CyPet (Nguyen, 2005). While avCFP has been proven as a useful fluorophore in multicolor labeling applications, and as the preferred Forster resonance energy transfer (FRET) donor to a YFP acceptor, its spectral properties limit its utility in some applications. Specifically, avCFP is relatively dim, has broad excitation and emission peaks (FIG. 2), and has a multi-exponential fluorescence lifetime. The multi-exponential fluorescence lifetime of avCFP complicates the use of this protein in fluorescence lifetime imaging (FLIM) applications. Some limitations have been partially addressed in the newer variants; Cerulean is twofold brighter and has a more homogenous fluorescence lifetime (Rizzo, 2004), while CyPet exhibits high FRET to the YFP variant YPet (Nguyen, 2005). However, despite these improvements, Cerulean and CyPet remain limited by fluorescent brightness that is less than 50% of the popular YFP variant Citrine (Shaner, 2005) and that is inferior to EGFP, and by fluorescence lifetimes that are poorly fit as single-exponentials, and a very broad fluorescence emission relative to other popular variants (FIG. 2) (Rizzo, 2004).

Thus, there is a need in the art for a fluorescent protein which mitigates the difficulties of the prior art.

SUMMARY OF THE INVENTION

In view of the problems associated with known fluorescent proteins, as described above, the inventors have engineered a novel non-oligomerizing CFP with a tyrosine-derived chromophore that has unexpectedly superior fluorescence properties, and have adopted the name 'teal fluorescent proteins (TFP)' with a preceding 'd' for dimeric or 'm' for monomeric, and a succeeding numerical identifier, to identify variants of the present invention.

Accordingly, in one aspect, the present invention provides an isolated nucleic acid sequence encoding a non-oligomerizing *Clavularia* teal fluorescent protein (TFP) variant having a tyrosine-derived chromophore. In certain embodiments, the nucleic-acid-sequence may be compatible with mammalian (e.g., human) codon usage. In one embodiment, the nucleic acid sequence has at least about 60% homology with the nucleotide sequence of SEQ ID NO: 2 or SEQ ID NO: 6. In another embodiment, the nucleic acid sequence has at least about 75% homology with the nucleotide sequence of SEQ ID NO: 2 or SEQ ID NO: 6. In still another embodiment, the nucleic acid sequence is substantially the same as, or identical to, the nucleotide sequence of SEQ ID NO: 2 or SEQ ID NO: 6. In another embodiment, the nucleic acid sequence is one that encodes the amino acid sequence of SEQ ID NO: 3 or SEQ ID NO: 7. Also provided is a fragment or derivative of the nucleic acid sequence of the invention. The present invention further provides an isolated nucleic acid, or mimetic or complement thereof, which hybridizes under stringent conditions to the nucleic acid sequence of the invention.

In another aspect, the present invention provides a method of engineering an isolated nucleic acid sequence encoding a non-oligomerizing *Clavularia* teal fluorescent protein (TFP) variant having a tyrosine-derived chromophore, by screening a fully-synthetic gene library. In one embodiment, the gene library comprises the nucleotide sequence of SEQ ID NO: 1.

In still another aspect, the present invention provides a vector that includes a nucleic acid sequence encoding a non-oligomerizing teal fluorescent protein (TFP) variant having a tyrosine-derived chromophore. In one embodiment, the vector is a plasmid. In another embodiment, the nucleic acid sequence of the vector is cDNA. Also provided is a host cell comprising the vector. The present invention further provides use of the vector in a method for expressing the nucleic acid sequence in mammalian cells. In one embodiment, the nucleic acid sequence is expressed as a tandem genetic fusion to another protein.

In a further aspect, the present invention provides a non-oligomerizing *Clavularia* teal fluorescent protein (TFP) variant that includes a tyrosine-derived chromophore, as well as any derivative, fragment, or homologue thereof. The *Clavularia* TFP variant may be a monomer or dimer. In one embodiment, the chromophore comprises the amino acid sequence tyrosine-glycine (YG). For example, the chromophore may comprise the amino acid sequence glutamine-tyrosine-glycine (QYG); the chromophore may also comprise the amino acid sequence alanine-tyrosine-glycine (AYG), or cysteine-tyrosine-glycine (CYG), or glycine-tyrosine-glycine (GYG).

In another embodiment, the TFP variant comprises at least one or more of the following mutations: histidine 42 replaced with asparagine; leucine 44 replaced with valine or isoleucine; serine 62 replaced with threonine; asparagine 63 replaced with threonine; glutamine 66 replaced with cysteine or glycine or alanine; leucine 72 replaced with phenylalanine; alanine 80 replaced with proline; aspartate 81 replaced with asparagine; arginine 123 replaced with histidine; phenylalanine 124 replaced with leucine; aspartate 125 replaced with lysine; methionine 127 replaced with lysine or glutamate; leucine 141 replaced with threonine; lysine 142 replaced with glycine; glutamate 144 replaced with aspartate; proline 145 replaced with alanine; isoleucine 149 replaced with arginine; leucine 1-50 replaced with methionine; valine 158 replaced with lysine; isoleucine 161 replaced with valine; serine 162 replaced with lysine; serine 164 replaced with lysine; tyrosine 173 replaced with histidine; cysteine 175 replaced with valine; serine 179 replaced with threonine; lysine 182 replaced with arginine; valine 186 replaced with alanine; leucine 213 replaced with valine; asparagines 216 replaced with serine; tyrosine 221 replaced with asparagine; glycine 224 replaced with aspartate; or serine 226 replaced with proline.

The TFP variant of the present invention may comprise an amino acid sequence having at least about 60% homology with the amino acid sequence of SEQ ID NO: 3 or SEQ ID NO: 7. In one embodiment, the TFP variant comprises an amino acid sequence having at least about 75% homology with the amino acid sequence of SEQ ID NO: 3 or SEQ ID NO: 7. In another embodiment, the TFP variant comprises an amino acid sequence which is substantially the same as, or identical to, the amino acid sequence of SEQ ID NO: 3 or SEQ ID NO: 7.

In one embodiment, the TFP variant of the present invention may have a fluorescence emission that is blue-shifted relative to wild-type cFP484 protein. In one embodiment, the TFP variant has a wavelength of maximum fluorescence emission that is less than about 504 nm. The TFP variant may also have an excitation spectrum ranging from about 350 to 500 nm and an emission spectrum ranging from about 450 to 600 nm. In one embodiment, the TFP variant has an excitation maximum ranging from about 450 to 460 nm and an emission maximum ranging from about 485 to 495 nm.

In yet another aspect, the present invention provides an antibody that specifically binds to the TFP variant of the invention. In one embodiment, the antibody is a polyclonal antibody; in another embodiment, the antibody is a monoclonal antibody.

In a further aspect, the present invention provides a tandem dimer comprising two TFP dimers, operatively linked by a peptide linker. In one embodiment, the tandem dimer comprises the amino acid sequence of SEQ ID NO: 5.

Additional aspects and advantages of the present invention will be apparent in view of the description, which follows. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which:

FIG. 3: Protein sequence alignments of mTFP1, coral CFPs, and relevant homologues. The aligned sequences are the designed synthetic gene library (SEQ ID NO: 8), mTFP1 (SEQ ID NO: 7), cFP484 from *Clavularia* sp. (Genbank accession AAF03374) (SEQ ID NO: 9), dsFP483 from *Discosoma striata* (Genbank accession AAF03370) (SEQ ID NO: 10), amFP486 from *Anemonia majano* (Genbank accession Q9U6Y6) (SEQ ID NO: 11), mCherry derived from *Discosoma striata* dsFP583 (Genbank accession AAV52164) (SEQ ID NO: 12) and EGFP derived from *Aequorea* GFP (SEQ ID NO: 13) (from Clontech vector pEGFP) (Shaner, 2004; Matz, 1999). Residues shaded cyan are changes or point mutations that were beneficial for mTFP1. Residues 66, 67, and 68 (enclosed in black box) are the precursors of the chromophore. Of the 227 structurally aligned residues of the 3 coral CFPs, there are 78 residues that are conserved in all 3 and an additional 91 residues that are conserved in 2 of the 3. Considering only those positions of two-thirds conservation, the inventors determined that cFP484 is the variant at 19%, dsFP483 at 34%, and amFP486 at 47% of the positions, and, cFP484 is the closest to the consensus sequence. The rationale behind the design of the gene library is summarized in Table 1. Numbering is consistent with DsRed and its monomeric variants that have no internal insertions or deletions relative to cFP484.

FIG. 4: Characterization of mTFP1 by Gel Filtration Chromatography. Gel filtration chromatography elution profile with detection at either 450 nm or 550 nm. The upper profile is a co-injection of dTFP0.2 and mCherry (Shaner, 2004) (a red monomer), the middle profile is dTomato (Shaner, 2004) (a red dimer) and mTFP1, and the lower profile is mTFP1 alone. The small 450 nm peak at the dimer elution volume is due to the weak absorbance of dTomato at this wavelength.

FIG. 5: pH-Dependence of the fluorescence emission of mECFP, mCerulean, and mTFP1. Each protein (stock solution of 1 mg/ml in 5 nm Tris pH 7) was diluted 1:100 in a 96-well plate containing 0.1 ml buffer (100 mM) at the indicated pH. Complete emission spectra at each pH were acquired in a plate reader equipped with monochromators.

FIG. 6: Relative rates of photo-bleaching of mECFP, mCerulean, and mTFP1. Photo-bleaching experiments were done directly on live colonies of E. coli on agar plates using the LED-based illumination system as described in the examples herein. Each data point represents the averaged mean fluorescence of 5 individual bacterial colonies expressing the indicated protein.

FIG. 7: Confocal fluorescence image of a Hela cell expressing mTFP1-actin (scale bar=10 μm). (A) HeLa cell expressing mTFP1-β-actin (scale bar=10 μm). (B) HeLa cell expressing mTFP1-α-tubulin (scale bar=10 μm).

FIG. 8: In vitro FRET responses for Cameleon (Miyawaki, 1997) constructs containing (A) mECFP, (B) mCerulean, and (C) mTFP1. For each protein the 3 spectra represent no $Ca^{2+}$ (red), 10 mM $Ca^{2+}$ (black), and no FRET (green). To obtain the 'no FRET' spectra, the linkers between the two fluorescent proteins were digested with trypsin under conditions where the fluorescent proteins themselves remain intact. The FRET efficiencies (E) in Table 1 were calculated using the formula E=1−(fluorescence at 490 nm before trypsin/fluorescence at 490 nm after trypsin).

FIG. 9: Fluorescence lifetime decay data for (A) mECFP, (B) mCerulean, and (C) mTFP1. Shown in each panel is the experimental data for the lifetime decay (open diamonds) and the instrument response function (IRF) for a scattering solution (open circles). The lifetime decay, convolved with the IRF, has been fitted with both single (green) and double (red) exponential decay functions. The inset is an expanded version of the region from 56 to 62 nm. For each protein, the residuals of the best fits are also shown. Excitation wavelength (nitrogen dye laser at 440 nm), emission wavelength (490 nm), and slits (1 nm) were the same for all experiments. Repeating the experiment under 'magic angle' conditions had no effect on the observed lifetimes.

FIG. 10A sets forth the complete DNA sequence of mTFP0.86 (SEQ ID NO:2) and 10B sets forth the complete DNA sequence of mTFP1 (or SEQ ID NO: 6).

FIG. 11 sets forth the complete DNA sequence of the synthetic gene library (SEQ ID NO:1). The synthetic gene library was digested with XbaI and BamHI, and ligated into pUC18 digested with the same enzymes. Transformation of E. coli with the ligated product gave at least 106 transformants. Plasmid DNA was prepared from the transformed E. coli, and digested with XhoI and EcoRI; the 736-bp fragment was then purified. This fragment was inserted into suitably-digested pBAD/HisB (Invitrogen) to create the final library suitable for expression and screening in colonies of E. coli strain LMG194.

FIG. 12A sets forth the complete protein sequence of mTFP0.86 (SEQ ID NO: 3) and 12B sets forth the complete protein sequence of mTFP1 (SEQ ID NO: 7).

FIG. 13 sets forth the complete DNA sequence of a tandem dimer of TFP, abbreviated as tdTFP0.3 (SEQ ID NO: 4).

FIG. 14 sets forth the complete protein sequence of tdTFP0.3 (SEQ ID NO: 5).

FIG. 15 shows the structure-based protein sequence alignment of the designed synthetic library (SEQ ID NO: 8), TFP (ClavCFP) (SEQ ID NO: 9), amFP486 (SEQ ID NO: 11), dsFP483 (SEQ ID NO: 10), dsFP583 (DsRed) (SEQ ID NO: 14), mRFP1 (SEQ ID NO: 15), and Aequorea GFP (avGFP) (SEQ ID NO: 16).

DETAILED DESCRIPTION OF PREFERRED EMBODIMENTS

Figure 1:
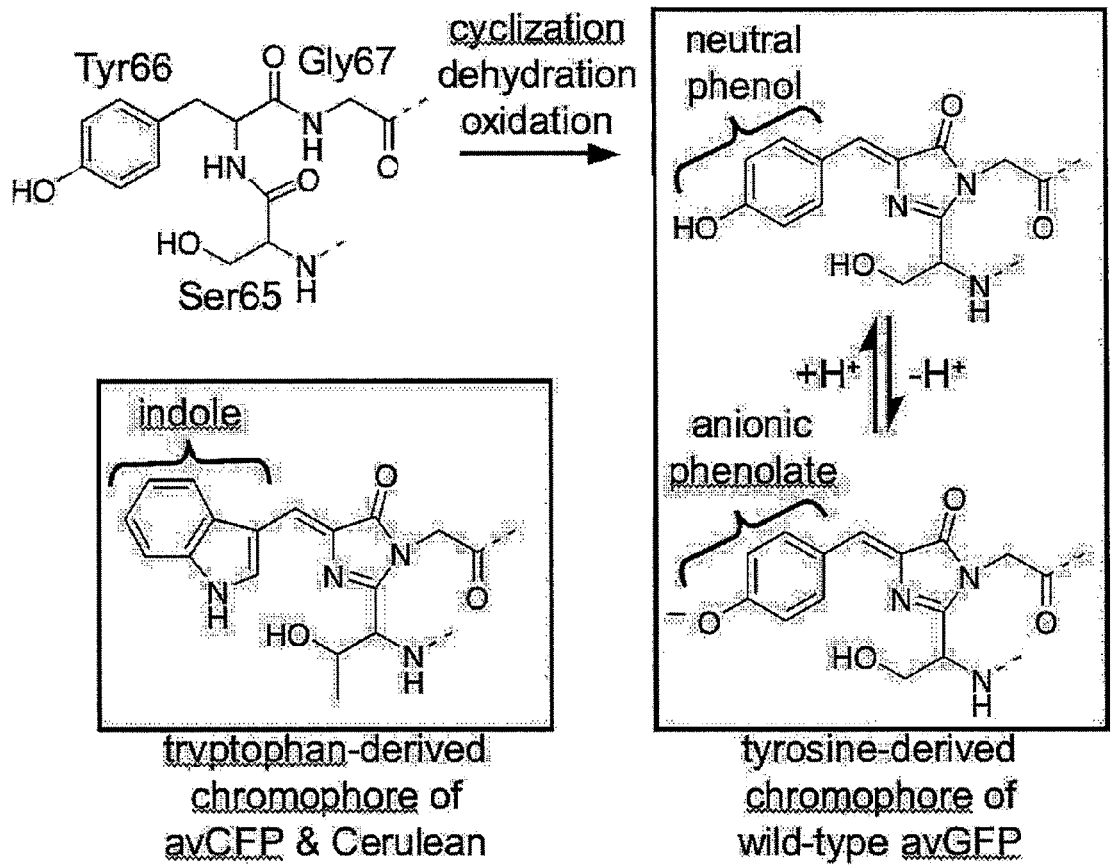
FIG. 1 (prior art) illustrates that, in wild-type avGFP, the green fluorescent chromophore arises from the post-translational modification of Ser65, Tyr66, and Gly67. The resulting chromophore contains either a neutral phenol or an anionic phenolate moiety. In avCFP and Cerulean, Tyr66 has been mutated to a tryptophan; thus, the resulting chromophore contains an indole moiety that is chemically distinct from either a phenol or phenolate group. TFP, a protein of the present invention, has a tyrosine-derived chromophore that differs from that of avGFP by the identity of the side chain at position 65, and the identity of the groups in near-spatial proximity to the fluorophore.
Figure 2:
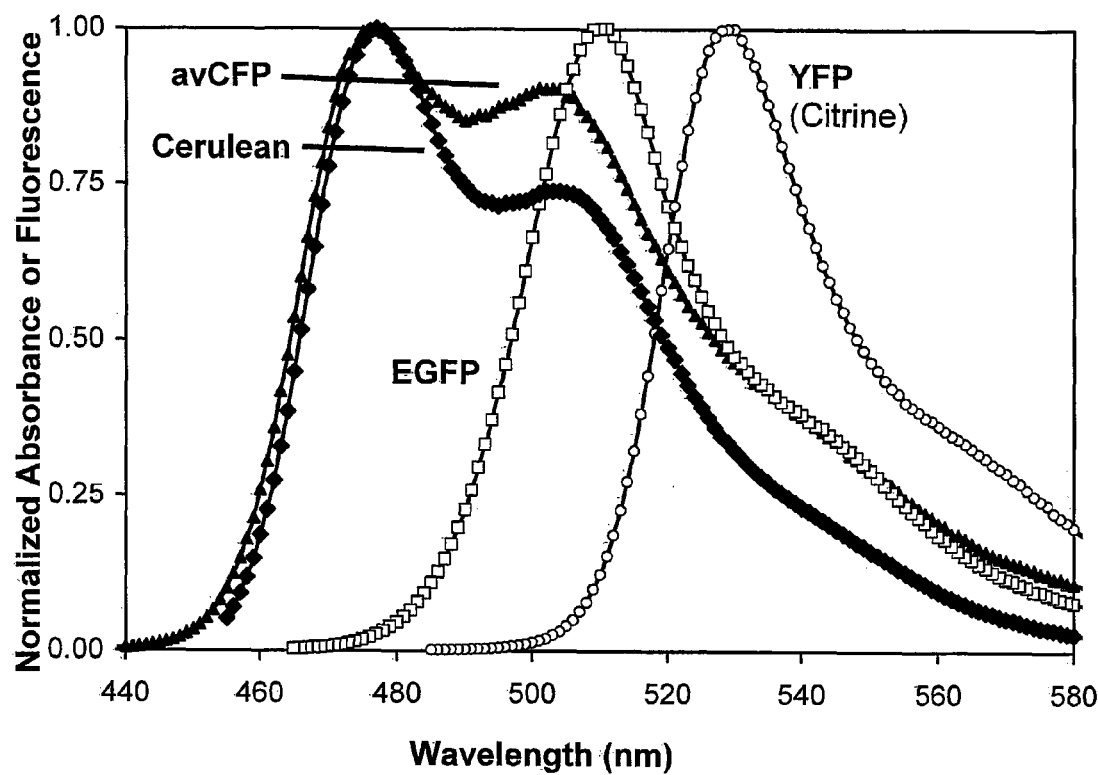
FIG. 2 (prior art) depicts the fluorescent emission spectra of avCFP, Cerulean, avGFP, and Citrine (a YFP). Note that both avCFP and Cerulean have strikingly broad emission peaks. A broad emission peak is undesirable when bandpass filters, which are typically used in fluorescence microscopy, are used to collect the fluorescence emission.

When describing the present invention, all terms not defined herein have their common art-recognized meanings. To the extent that the following description is of a specific embodiment or a particular use of the invention, it is intended to be illustrative only, and not limiting of the claimed invention. The following description is intended to cover all alternatives, modifications and equivalents that are included in the spirit and scope of the invention, as defined in the appended claims.

Aspects of the present invention relate to novel proteins from a naturally occurring protein that fluoresces at cyan wavelength to create a variant that is optimized for use in fluorescence imaging. Three naturally occurring homologues of Aequorea GFP (cFP484 from Clavularia sp., amFP486 from Anemonia majano, and dsFP483 from Discosoma striata) with tyrosine-derived chromophores and emission peaks between ~480-490 nm that had been identified in coral (Matz, 1999) were initially considered.

As used-herein, the terms "CFP" and "cyan fluorescent protein" refer to any GFP homologue with a fluorescence emission peak at less than or equal to 495 nm. As further used herein, a prefix is added to "CFP", when referring to CFPs from specific organisms, to indicate the name of the organism from which the gene encoding the protein was originally derived. As an example, as used herein, the term "cFP484" refers to a fluorescent protein ("FP") of the species *Clavularia* sp. ("c") with a major emission maximum of 484 nm. The term "TFP" or "teal fluorescent protein" refers to a CFP of the present invention, having a tyrosine derived chromophore.

To identify amino acid positions of TFP, a numbering system is used in which the N-terminal residue is labeled 1, the second residue from the N-terminus is labeled 2, and so until the last residue of the protein is reached at the C-terminus. If residues are added or deleted from the N-terminus of the protein, the identity of each subsequent residue could change if consistently numbered from the N-terminus. Therefore, employed herein, was a numbering system in which the residues of the chromophore-forming residues in the wild-type protein are glutamine 66, tyrosine 67, and glycine 68. Preceeding and subsequent amino acids were labeled consistently with the chromophore numbering amino acids.

The naturally occurring homologues of *Aequorea* GFP mentioned above have emission peak shapes and fluorescent brightness comparable to *Aequorea* GFP and are likely tetramers and unsuitable for use as non-perturbing genetic labels (Campbell, 2002). In one example, the inventors chose cFP484 (International Application Publication No. WO0127150; Matz 1999) as the template from which to initiate the directed evolution. cFP484 is a preferred starting point as it is the least divergent from a hypothetical 'consensus' sequence (FIG. 3); it has the highest fluorescent brightness; and it has a single cysteine residue while dsFP483 and amFP486 each have five (Matz, 1999).

To prepare proteins of the current invention, a fully-synthetic designed gene library with a theoretical diversity of ~5×105 cFP484 variants (Table 1) was prepared; followed by screening. Such an approach has not been previously used for fluorescent proteins. In previous work, genes have been resynthesized with human codon usage. Libraries of gene variants have then been created by random mutation of the gene, or targeted diversification at specific positions within the gene.

TABLE 1

Rationale for design of the synthetic gene library

| Residue number | Mutated to | Codon | Rationale |
|---|---|---|---|
| His42 | His, Asn, Gln, Lys | MAS | Mutations beneficial to tetrameric DsRed variants (Bevis, 2002). Not conserved in coral CFPs. |
| Leu44 | Leu, Val, Ala, Pro | SYC | Mutations beneficial to tetrameric DsRed variants (Bevis, 2002). Not conserved in coral CFPs. |
| Gln66 (residue of chromophore) | Gln, Lys, Met, Leu | MWG | Mutations beneficial to *Aequorea* GFP (Heim, 1995) and monomeric RFPs (Shaner, 2004). Lys or Gln present in coral CFPs. |
| Arg70 | Lys, Arg | ARG | Mutations beneficial to monomeric RFPs (Campbell, 2002). Lys or Arg present in coral CFPs. |
| Ala71 | Ala, Val | GYC | Mutations beneficial to monomeric RFPs (Campbell, 2002). Ala or Cys present in coral CFPs. |
| Leu72 | Leu, Phe, Ile | HTC | Phe in 2 coral CFPs and Leu in 1 coral CFP. |
| Phe83 | Leu, Phe, Ile | HTC | Mutations beneficial to monomeric RFPs (Campbell, 2002; Shaner, 2004). Phe in 2 coral CFPs and Leu in 1 coral CFP. |
| Ile104 | Ile, Thr | AYC | May disrupt A–B interface interactions |
| Phe124 | Leu, Phe, Ile | HTC | Mutations beneficial to dimeric RFPs (Campbell, 2002). Strict conservation in coral CFPs. |
| Asp125 | Lys, Arg | ARG | Likely to disrupt A–B interface interactions. |
| Met127 | Lys, Arg | ARG | Likely to disrupt A–B interface interactions. |
| Met150 | Met, Leu | MTG | Mutations beneficial to monomeric RFPs (Campbell, 2002). Met in 2 coral CFPs and Leu in 1 coral CFP. |
| His163 | His, Gln | CAS | Mutations beneficial to dimeric and monomeric RFPs (Campbell, 2002; Shaner, 2004). His in 2 coral CFPs and Ala in 1 coral CFP. |
| Ser179 | Ser, Thr | WCC | Mutations beneficial to dimeric RFPs (Campbell, 2002). Thr in 2 coral CFPs and Ser in 1 coral CFP. |

Preferred features of the library included: mammalian codon usage, deletion of 40 non-homologous residues from the N-terminus, addition of the 7 N-terminal and 7 C-terminal residues of *Aequorea* GFP, semi-degenerate codons encoding potential 'tetramer-breaking' mutations at 3 external positions, and semi-degenerate codons encoding potential 'rescuing' mutations at 11 internal positions. Sequencing of random clones revealed that 12% of the genes had mutations only at desired positions and that the true library diversity was ~4×106 variants. The library was used to transform *E. coli* and the resulting colonies were screened for fluorescence. Fluorescent colonies represented ~0.5% of all colonies and were approximately equally divided between colonies that fluoresced at 490 nm and colonies that fluoresced at ~510 nm. The most brightly fluorescent protein identified after extensive screening was a dimer with 8 mutations relative to wild type and an emission peak at 486 nm. These proteins have been described herein as 'teal fluorescent protein' (TFP), with a preceding 'd' for dimeric or 'm' for monomeric, and a succeeding numerical identifier, to identify variants described herein. Following this convention, the dimeric protein identified in the initial screen was designated dTFP0.1 and the 170% brighter version resulting from one round of directed evolution was designated dTFP0.2 (Table 2 and 3). Substitution of dimer interface residues Ser162 and Ser164 with lysine produced a monomeric version (FIG. 4), mTFP0.3, which retained only 15% of the brightness of its dimeric precursor. After multiple successive rounds of screening libraries (generated by random or saturation mutagenesis) for variants with improved brightness and high 480/530 nm emission ratio, mTFP0.7 was obtained that had a fluorescent brightness equivalent to Cerulean (Table 2). However, imaging an mTFP0.7-actin fusion in live HeLa cells by confocal microscopy, led to a fluorescent signal that rapidly vanished upon illumination with the 458 μm laser, due to a rapid in vitro photo-conversion to a non fluorescent state (Table 2 and 3).

TABLE 2

Fluorescent properties of CFPs and TFPs.

| Protein | Absorbance (nm) | Emission (nm) | $\epsilon^a * 10^{-3}$ (mM$^{-1}$ cm$^{-1}$) | $\Phi^b$ | Brightness$^c$ (mM$^{-1}$cm$^{-1}$) | pKa | Photostability$^d$ | Cameleon FRET efficiency (+/− Ca$^{2+}$) − | + |
|---|---|---|---|---|---|---|---|---|---|
| cFP484$^e$ | 456 | 484 | 35.3 | 0.48 | 17 | ND$^f$ | ND | ND | ND |
| dTFP0.1 | 456 | 485 | 42 | 0.63 | 26 | ND | <1 | ND | ND |
| dTFP0.2 | 456 | 486 | 60 | 0.68 | 41 | ND | <1 | ND | ND |
| mTFP0.3 | 458 | 488 | 19 | 0.31 | 6 | ND | <1 | ND | ND |
| mTFP0.7 | 453 | 488 | 60 | 0.50 | 30 | 4.0 | <1 | ND | ND |
| mTFP1 | 462 | 492 | 64 | 0.85 | 54 | 4.3 | 163$^g$/110$^h$ | 39% | 49% |
| mECFP | 433/451$^i$ | 475/504$^i$ | 33/30$^i$ | 0.41 | 13/12$^i$ | 4.7 | 64$^{h,j}$ | 26% | 39% |
| mCerulean | 433/451$^i$ | 475/503$^i$ | 43/37$^i$ | 0.64 | 27/24$^i$ | 4.7 | 36$^{g,j}$ | 30% | 41% |
| EGFP$^j$ | 488 | 507 | 56 | 0.60 | 34 | 6 | 174$^{h,j}$ | ND | ND |
| tdTFP0.3 | 458 | 489 | 125 | 0.69 | 86 | ND | ND | ND | ND |

$^a$Extinction coefficient.
$^b$Quantum yield.
$^c$Product of $\Phi$ and $\epsilon * 10^{-3}$. Values for common FP variants have been previously tabulated (Shaner, 2005).
$^d$Time to bleach from an initial emission rate of 1000 photons/s to 500 photons/s.
$^e$Values from ref. (Matz, 1999).
$^f$Not determined.
$^g$Measured with 10% ND filters.
$^h$Measured with no ND filters.
$^i$Values for both 'humps' of mECFP and mCerulean are provided.
$^j$Values from ref. (Shaner, 2005).

TABLE 3

Mutations in dimeric and monomeric TFP variants.

| Variant | Library construction strategies | Mutations |
|---|---|---|
| dTFP0.1 | See Supplementary Table 1. | Inside: H42N, L44V, L72F, F124L, M150L, S179T A–B interface: D125K, M127K |
| dTFP0.2 | 2 generations of random mutagenesis. | Inside: D81N Outside: S226P |
| mTFP0.3 | Site-directed mutagenesis at 162 and 164. Saturation mutagenesis at 163. | A–C interface: S162K, S164K |
| mTFP0.4 | Saturation mutagenesis at 66. Semi-saturation mutagenesis at 175. | Inside: Q66C, C175V |
| mTFP0.5 | 3 generations of random mutagenesis. | Inside: S62T, C66G Outside: A80P, N216S A–B interface: K127E, K182R |
| mTFP0.6 | Saturation mutagenesis at 66 + 163, 66 + 197. Semi-saturation mutagenesis at 66 + 147, 66 + 213. | Inside: G66A, L213V Outside: S2N Replace 223–228 with TG |
| mTFP0.7 | 2 generations of random mutagenesis. | Inside: V44I, Y173H Outside: V186A A–B interface: R123H Mutate: N2S |
| mTFP0.8 | Semi-saturation mutagenesis at 62, 63, 64, 65, and 66 with screening for photostability. | Inside: N63T |
| mTFP0.9 | Semi-saturation mutagenesis at 142, 144, 145, 149, 150, and 161 with screening for photostability. | Inside: K142G, L150M (reversion to wild type), I161V A–C interface: E144D, P145A, I149R |
| mTFP1 | 2 generations of random mutagenesis with screening for photostability. | Outside: L141T, V158K, Y221N, G224D |

To select for photostable variants, an array of six 460 nm light emitting diodes (Lumileds, San Jose, Calif.) was constructed that provided even illumination of a Petri dish with ~55 mW/cm2; an irradiance that is 1400× more intense than the excitation used in previous screening and sufficient to photoconvert mTFP0.7 within seconds. The fluorescence of libraries of mTFP0.7 variants expressed in bacterial colonies was digitally imaged during exposure to intense illumination and colonies with decreased propensity to photoconvert were identified. Following several rounds of selection for variants that were photostable, bright, and retained a high 480/530 nm emission ratio, we arrived at mTFP1 that has a total of 29 mutations relative to wild type protein. In addition, mTFP1 is 2-fold brighter and more photostable than Cerulean and is insensitive to physiologically relevant changes in pH (Table 2 and FIGS. 5 and 6).

To determine the photostability of mTFP1, photobleaching experiments were done on droplets of purified protein suspended in mineral oil following the protocol of Shaner et al. (Shaner, 2005). This method is designed to approximate the conditions of a typical wide-field microscopy experiment while rigorously accounting for differences in the spectral properties of the fluorescent proteins as well as the optical properties of the microscope. Using this method, the time for bleaching from an initial emission rate of 1,000 photons/sec/molecule down to 500 photons/sec/molecule (t1/2) was determined to be 163 s when 10% neutral density filters were used. With no neutral density filters the t1/2 was 110 s for mTFP1. For the sake of comparison, the t1/2 for Cerulean with 10% neutral density filters is 36 s and the t1/2 for EGFP with no neutral density filters is 174 s (Shaner, 2005). As previously herein (Shaner, 2005), Cerulean displays an illumination intensity-dependent fast bleaching component that can decrease the intensity to 60% of its initial value within the first few seconds of imaging under typical conditions (Shaner, 2005 and P. Steinbach, personal communication). No fast bleaching component was observed for mTFP1.

Expression of mTFP1-actin fusion in mammalian cells was performed to demonstrate its suitability for use as non-perturbing fusion partner (FIG. 7). The fusion protein localized correctly and there was no significant decrease in intensity upon illumination with the 458 nm laser.

Typical fluorescence filter sets used to image Cerulean are adequate but suboptimal for mTFP1. In one embodiment, to take advantage of mTFP1's improved brightness, a 445/30 nm excitation filter, a 470 nm beamsplitter, and a 495/30 nm emission filter may be used (FIG. 7B and Table 4). This combination gives a 2.6-fold increase in fluorescent signal relative to mCerulean imaged using a standard CFP set (e.g. a 436/20 nm excitation filter, a 455 nm beamsplitter, and a 480/40 nm excitation filter). This preferred set has been used in combination with a new YFP emission filter (545/30 nm), to demonstrate that mTFP1-YC3.3 can be practically employed in live cell FRET imaging. The gene encoding mTFP1-YC3.3 was cloned into a mammalian expression vector with an N-terminal signal sequence and a C-terminal endoplasmic reticulum (ER) retention peptide (Miyawaki, 1997). FRET imaging of transiently transfected HeLa cells on an Zeiss Axiovert 200M equipped with a digital CCD camera revealed a typical pattern of endoplasmic reticulum localization and robust ratiometric responses to induced changes in the free Ca2+ concentration. This result demonstrates that the spectral distinction between mTFP1 and mCitrine are sufficient for these proteins to be used as an advantageous new FRET pair that can be imaged on a standard epifluorescence microscope equipped with appropriate bandpass filter sets.

TABLE 4

Experimentally determined relative fluorescence intensities for identical concentrations of mTFP1, mCerulean, and mCitrine imaged on an epi-fluorescence microscope with xenon arc lamp illumination.

| Protein | Excitation filter[a] | Beamsplitter[a] | Intensity relative to mCerulean imaged with a HQ436/20 excitation filter and D480/40 emission filter[a] | |
|---|---|---|---|---|
| | | | D480/40 | HQ495/30 |
| mTFP1 | D436/20 | 455DCLP | 1.3 | 1.5 |
| | HQ445/30 | 470DCXR | ND[b] | 2.6 |
| mCerulean | D436/20 | 455DCLP | 1.0 | 0.8 |
| | HQ445/30 | 470DCXR | ND[b] | 1.3 |

| Protein | Excitation filter[a] | Beam-splitter[a] | TFP or CFP emission filter[a] | Relative intensity passed by YFP emission filter[a,c] | |
|---|---|---|---|---|---|
| | | | | HQ535/30 | HQ545/30 |
| mTFP1 | D436/20 | 455DCLP | HQ495/30 | 0.39 | 0.30 |
| | HQ445/30 | 470DCXR | HQ495/30 | 0.39 | 0.30 |
| mCerulean | D436/20 | 455DCLP | D480/40 | 0.35 | 0.30 |
| | HQ445/30 | 470DCXR | HQ495/30 | 0.41 | 0.34 |
| mCitrine | HQ500/20 | Q515LP | ND[b] | 1 | 0.91 |
| | D436/20 | 455DCLP | ND[b] | 0.12 | 0.07 |
| | HQ445/30 | 470DCXR | ND[b] | 0.15 | 0.09 |

[a]All filters and beamsplitters were purchased from Chroma Technology Corp. Filters are designated with Chroma part numbers.
[b]Not determined.
[c]For mTFP1 and mCerulean, intensities are relative to the intensity in the indicated TFP or CFP emission channel. For mCitrine, all intensities are relative to the intensity obtained with a HQ500/20 excitation filter and HQ535/30 emission filter.

mTFP1's suitability as a FRET donor to Citrine was also demonstrated. Analogous versions of yellow Chameleon 3.3 (YC3.3) containing either mECFP, mCerulean, or mTFP1 were constructed and their FRET efficiency in the absence and presence of Ca2+ was determined (Table 2). FRET efficiencies were accurately determined by trypsinolysis under conditions where the fluorescent proteins themselves remain intact but the calmodulin-M13 domain is cleaved. FRET efficiencies (E) for mECFP and mCerulean in Table 2 were calculated using the formula E=1-(fluorescence at 475 nm before trypsinization/fluorescence at 475 nm after trypsinization). For mTFP1, the fluorescence before and after trypsinization was measured at 490 nm. All three reporters increased FRET efficiency upon Ca2+-binding but the mTFP1 version was notable for its significantly higher efficiencies in both the Ca2+-bound and Ca2+-free states. The trend in experimental FRET efficiencies, mECFP<mCerulean<mTFP1, is consistent with our calculated Ro values of 5.0 nm for mECFP, 5.3 nm for mCerulean, and 5.7 nm for mTFP1. It is important to note that the original YC3.3 contained ECFP and had been optimized for maximum FRET difference between the Ca2+-bound and Ca2+-free states. It is therefore unsurprising that switching to an mTFP1 donor (with a different dipole orientation and increased Ro value) results in a slightly decreased dynamic range. This is almost certainly because the protein was empirically optimized (Miyawaki, 1997 and 2000) for interfluorophore distance changes centered on the Ro of ECFP (where there is the strongest dependence of FRET efficiency on distance). It is believed that if mTFP1-YC3.3 was to be subject to similar systematic optimization, the dynamic range will be significantly improved.

Finally, the utility of mTFP1 for use in fluorescence lifetime imaging (FLIM) was demonstrated by measuring the fluorescence lifetimes of mECFP, mCerulean, and mTFP1 under identical in vitro conditions (FIG. 8). In contrast to mCerulean, which is best described as a poor fit of a single lifetime (Rizzo, 2004), mTFP1 is unambiguously best fit as single lifetime ($\tau=3.3$ ns, $\chi^2=1.1$). Attempts to fit the mTFP1 lifetime decay data with a double exponential converged to solution in which $\tau_1=\tau_2=3.2$ ns; strong evidence for the single fluorescent lifetime. Repeating the experiment under 'magic angle' conditions had no effect on the observed lifetimes or statistics. Analogous experiments with mECFP and mCerulean resulted in data that was best fit as double exponentials (for mECFP $\tau_1=3.7$ ns (80%), $\tau_2=1.7$ ns (20%), $\chi^2=1.1$; for mCerulean c=3.7 ns (80%), $\tau_2=1.9$ ns (20%), $\chi^2=0.99$). As previously reported (Rizzo, 2004), mCerulean could also be adequately fit with a single exponential ($\tau=3.5$ ns, $\chi^2=1.1$), though the residuals were consistently unsatisfactory.

The approach described herein is advantageous in that it permits the discovery of mutants with combinations of mutations that are only beneficial when they occur together. Such variants could not be discovered by a stepwise approach, since it is possible that the individual mutations are not beneficial (or might even be detrimental) by themselves. For example, dTFP0.1 contains six mutations (H42N, L44V, L72F, F124L, M150L, S179T) in the interior of the protein. Through the use of random mutagenesis, such a combination of mutations would be so exceptionally rare that it would never be discovered by any sort of conventional library screening procedure. In addition, even six rounds of random mutagenesis (with an average of one mutation per gene in each round) would probably not lead to this same variant, unless each mutation in isolation resulted in an improvement.

The engineered proteins described herein differ from the wild-type protein in a number of respects. For example, the proteins of the present invention are monomers, and are brighter than the wild-type protein. The proteins also lack the first forty amino acids of cFP484, and the long N-terminal sequence of cFP484. Furthermore, the monomeric versions of TFP described herein lack the last six amino acids of cFP484. The corresponding sequences of *Aequorea* GFP have been appended to the N- and C-termini of the TFP variants.

The chromophore of cFP484, from which the monomers of the present invention were ultimately derived, was obtained from the amino acid sequence glutamine-tyrosine-glycine (QYG). The tyrosine and glycine are absolutely essential, and are present in all naturally-occurring fluorescent proteins of all colors. The preceding residue, glutamine, is also very important, but tends to vary among different colors. Nevertheless, different proteins of the same color can have different residues at this position. For example, the other two naturally-occurring cyan fluorescent proteins have a glutamine at this position. In certain of the monomers of the present invention, mutations have been introduced at this position, and particular residues have been found to be preferable to the wild-type glutamine residue. By way of example, mTFP0.4 has a cysteine, mTFP0.5 has a glycine, and mTFP0.1 has an alanine.

Tryptophan residues located in the vicinity of the chromophore sequence do not have a particular significance with respect to the chromophore structure. The engineered cyan fluorescent proteins, avCFP and Cerulean, have a chromophore structure that is derived from the sequence threonine-tryptophan-glycine.

The proteins of the present invention are advantageous, relative to cFP484, in that: (1) they are monomers; (2) they have a higher extinction coefficient; (3) they have a higher quantum yield; (4) they have mammalian codon usage; (5) high brightness; (6) improved photostability; (7) efficient intra- and inter-molecular FRET with a yellow or orange acceptor fluorescence protein; (8) dual color imaging in combination with an orange or red fluorescent protein and (9) a single fluorescence lifetime. For dual color imaging in combination with a YFP, mTFP1 could provide a brighter fluorescent signal than existing *Aequorea*-derived CFPs but the bleedthrough into the acceptor emission channel may be only slightly better (or possibly worse) depending on the specific filter combination in place. In addition, these proteins have N- and C-terminal sequences corresponding to the N- and C-terminal sequences of *Aequorea* GFP. This facilitates subcloning, since any DNA primer that can be used to perform PCR on the widely-available *Aequorea* GFP will also work with the TFPs of the present invention. These proteins are also optimized for expression at 37° C., and may have lower toxicity to live cells. Furthermore, these proteins have a narrow emission peak; this is advantageous, relative to *Aequorea*-derived CFP. It is believed that these proteins will be useful in research, particularly in the areas of cell biology, physiology, oncology, and biochemistry.

In view of the foregoing, the present invention provides an isolated nucleic acid composition comprising a nucleic acid sequence encoding a non-oligomerizing *Clavularia* teal fluorescent protein (TFP) variant having a tyrosine-derived chromophore. Also provided is any fragment or derivative of the isolated nucleic acid composition of the invention. The complete DNA sequence of *Clavularia* sp. fluorescent protein FP484 may be obtained from Accession No. AF168424.

The recently reported crystal structure of amFP486 revealed the presence of a positively charged histidine near the chromophore that may limit charge transfer in the excited state and thereby give rise to the blue-shift [44]. Arg70, Glu148, His197, and Glu215. Without being bound by a theory, it is likely that the Arg/Lys degeneracy at position 70 was responsible for the 50/50 split between green and cyan FPs in the initial library.

As used herein, a "nucleic acid" or "polynucleotide" includes a nucleic acid, an oligonucleotide, a nucleotide, a polynucleotide, and any fragment, variant, or derivative thereof. The nucleic acid or polynucleotide may be double-stranded, single-stranded, or triple-stranded DNA or RNA (including cDNA), or a DNA-RNA hybrid of genetic or synthetic origin, wherein the nucleic acid contains any combination of deoxyribonucleotides and ribonucleotides and any combination of bases, including, but not limited to, adenine, thymine, cytosine, guanine, uracil, inosine, and xanthine hypoxanthine. The nucleic acid or polynucleotide may be combined with a carbohydrate, a lipid, a protein, or other materials. A nucleic acid sequence of interest may be chemically synthesized using one of a variety of techniques known to those skilled in the art, including, without limitation, automated synthesis of oligonucleotides having sequences which correspond to a partial sequence of the nucleotide sequence of interest, or a variation sequence thereof, using commercially-available oligonucleotide synthesizers, such as the Applied Biosystems Model 392 DNA/RNA synthesizer.

One nucleic acid composition of the present invention is the nucleotide sequence encoding mTFP0.86 (SEQ ID NO: 2; FIG. 10A). Another nucleic acid composition comprises the sequence encoding mTFP1 (SEQ ID NO: 6, FIG. 10B). Accordingly, in one embodiment of the present invention, the isolated nucleic acid composition comprises a nucleic acid sequence having at least about 60% homology with the nucleotide sequence of SEQ ID NO: 2 or SEQ ID NO: 6. In another embodiment of the present invention, the isolated nucleic acid composition comprises a nucleic acid sequence having at least about 75% homology with the nucleotide sequence of SEQ ID NO: 2 or SEQ ID NO: 6. In still another embodiment of the present invention, the isolated nucleic acid composition comprises a nucleic acid sequence that is substantially the same as, or identical to, the nucleotide sequence of SEQ ID NO: 2 or SEQ ID NO: 6. In one embodiment, the nucleic acid composition comprises any nucleic acid sequence which encodes any protein of the present invention, including proteins having the ammo acid sequence SEQ ID NO: 3 or SEQ ID NO: 7. In certain embodiments, the nucleic acid sequence may be re-synthesized such that it is compatible with mammalian (e.g., human) codon usage, or the sequence may be resynthesized to be optimised for non-mammalian codon preferences.

The present invention further provides an isolated nucleic acid, including any mimetic or complement thereof, that hybridizes under stringent conditions to the nucleic acid composition described herein. The "complement" of a nucleic acid sequence refers, herein, to a nucleic acid molecule which is completely complementary to another nucleic acid, or which will hybridize to the other nucleic acid under conditions of stringency. Stringent (e.g., high-stringency) conditions are known in the art (see, e.g., Maniatis, 1989; Ausubel, 2001). Stringent conditions are sequence-dependent, and may vary depending upon the circumstances.

The present invention further provides a method of engineering a nucleic acid sequence encoding a non-oligomerizing *Clavularia* teal fluorescent protein (TFP) variant having a tyrosine-derived chromophore, by screening a fully-synthetic gene library. In one embodiment, the gene library comprises the nucleotide sequence of SEQ ID NO: 1 (FIG. 11).

The present invention also provides a vector comprising a nucleic acid sequence encoding a non-oligomerizing *Clavularia* teal fluorescent protein (TFP) variant having a tyrosine-derived chromophore. Also provided is a host cell (e.g., a mammalian cell) comprising the vector.

In one embodiment of the present invention, the vector is a plasmid, although it is to be understood that other types of vectors, such as cosmids and phagemids, may also be used for the purposes of the present invention. The term "plasmid", as used herein, refers generally to circular double-stranded DNA, which is not bound to a chromosome. The DNA may be a chromosomal or episomal-derived plasmid. The plasmid of the present invention may optionally contain a terminator of transcription; a promoter; and/or a discrete series of restriction-endonuclease recognition sites, located between the promoter and the terminator. In the plasmid, a polynucleotide insert of interest (e.g., one encoding a non-oligomerizing *Clavularia* teal fluorescent protein (TFP) variant having a tyrosine-derived chromophore) should be operatively linked to an appropriate promoter, such as its native promoter or a host-derived promoter, such as the *E. coli* lacZ promoters, the trp and tac promoters, the τ3 and τ7 promoters, or the CMV promoters. Other suitable promoters will be known to the skilled artisan.

The vector of the present invention may comprise cDNA encoding a non-oligomerizing *Clavularia* teal fluorescent protein (TFP) variant having a tyrosine-derived chromophore. As used herein, the term "cDNA" refers to an isolated DNA polynucleotide or nucleic-acid molecule, or any fragment, derivative, or complement thereof. The cDNA may be double-stranded, single-stranded, or triple-stranded, it may have originated recombinantly or synthetically, and it may represent coding and/or noncoding 5' and/or 3' sequences.

The vector of the present invention may be useful in a method for expressing the nucleic acid sequence in mammalian cells or non-mammalian cells. In one embodiment, the nucleic acid of the vector is expressed as a tandem genetic fusion to another protein.

The present invention further provides a non-oligomerizing *Clavularia* teal fluorescent protein (TFP) variant comprising a tyrosine-derived chromophore, as well as any derivative, fragment, or homologue thereof. The amino acid sequence of *Clavularia* sp. fluorescent protein FP484 may be obtained from Accession No. AF168424. The TFP variant of the present invention may be a monomer or a dimer.

In one embodiment of the present invention, the TFP variant includes a chromophore comprising the amino acid sequence tyrosine-glycine (YG). By way of example, the chromophore may comprise the amino acid sequence glutamine-tyrosine-glycine (QYG); the chromophore may also comprise the amino acid sequence cysteine-tyrosine-glycine (CYG), glycine-tyrosine-glycine (GYG), or alanine-tyrosine-glycine (AYG), as in variants mTFP0.7, mTFP0.75, and mTFP0.86, respectively.

Furthermore, the TFP variant of the present invention may comprise an amino acid sequence having at least about 60% homology with the amino acid sequence of SEQ ID NO: 3 or SEQ ID NO: 7 (FIGS. 12A and 12B). In one embodiment, the TFP variant comprises an amino acid sequence having at least about 75% homology with the amino acid sequence of SEQ ID NO: 3 or SEQ ID NO: 7. In another embodiment, the TFP variant comprises an amino acid sequence, which is substantially the same as, or identical to, the amino acid sequence of SEQ ID NO: 3 or SEQ ID NO: 7. The TFP variant of the present invention may also comprise at least one of the following mutations: H42N, L44V, L72F, F124L, M150L, and S179T.

As discussed above, the inventors' variant proteins are advantageous in that they exhibit enhanced brightness. The TFP variant of the present invention may have a fluorescence emission that is blue-shifted relative to the wild-type cFP484 protein. In one embodiment, the TFP variant of the present invention has a wavelength of maximum fluorescence emission that is less than about 504 nm. In another embodiment, the TFP variant of the present invention has an excitation spectrum ranging from about 350 to 500 nm and an emission spectrum ranging from about 450 to 600 nm. In still another embodiment, the TFP variant has an excitation maximum ranging from about 450 to 460 nm and an emission maximum ranging from about 485 to 495 nm.

The present invention further provides a tandem dimer comprising two TFP dimers, operatively linked by a peptide linker. Thus, the dimers may be fused into a single non-oligomerizing gene product.

An exemplary tandem dimer of the present invention is tdTFP0.3. Accordingly, in one embodiment of the present invention, the tandem dimer is encoded by a DNA sequence comprising the nucleotide sequence of SEQ ID NO: 4 (FIG. 13). In another embodiment of the present invention, the tandem dimer comprises the protein sequence of SEQ ID NO: 5 (FIG. 14).

Additionally, the present invention provides an antibody that specifically binds to a TFP variant, as described herein. The antibody of the present invention may be polyclonal or monoclonal, and may be produced by techniques well known to those skilled in the art. Polyclonal antibody, for example, may be produced by immunizing a mouse, rabbit, or rat with purified protein. Monoclonal antibody then may be produced by removing the spleen from the immunized mouse, rabbit, or rat, and fusing the spleen cells with myeloma cells to form a hybridoma which, when grown in culture, will produce a monoclonal antibody.

The antibodies used herein may be labelled with a detectable marker or label. Labelling of an antibody may be accomplished using one of a variety of labelling techniques, including peroxidase, chemiluminescent labels known in the art, and radioactive labels known in the art. The detectable marker or label of the present invention may be, for example, a non-radioactive or fluorescent marker, such as biotin, fluorescein (FITC), acridine, cholesterol, or carboxy-X-rhodamine, which can be detected using fluorescence and other imaging techniques readily known in the art. Alternatively, the detectable marker or label may be a radioactive marker, including, for example, a radioisotope. The radioisotope may be any isotope that emits detectable radiation. Radioactivity emitted by the radioisotope can be detected by techniques well known in the art. For example, gamma emission from the radioisotope may be detected using gamma imaging techniques, particularly scintigraphic imaging.

The present invention is described in the following Examples, which are set forth to aid in the understanding of the invention, and should not be construed to limit in any way the scope of the invention as defined in the claims which follow thereafter.

EXAMPLES

Example 1

General Methods and Materials

The synthetic gene library of *Clavularia* cFP486 variants was commissioned from the DNA Technologies Unit at the NRC Plant Biotechnology Group (Saskatoon, SK). All synthetic DNA oligonucleotides for cloning and construction of subsequent libraries were purchased from Sigma-Genosys Canada (Oakville, ON). PCR products and products of restriction digest were routinely purified using the QIAquick PCR-purification kit according to the manufacturers protocols (Qiagen). Restriction enzymes were purchased from either Invitrogen or New England Biolabs. The cDNA sequences for all TFP variants and fusion constructs was confirmed by dye terminator cycle sequencing using the DYEnamic ET kit (Amersham Biosciences). Sequencing reactions were analyzed at the University of Alberta Molecular Biology Service Unit. The proteins mECFP and mCerulean have the A206K mutation in addition to their characteristic substitutions (Zacharias, 2002; Rizzo, 2004 and 2005).

Example 2

Selection of the Starting Template

Prior to the present invention, there were three reported naturally-occurring fluorescent proteins with tyrosine-derived chromophores and wavelengths of maximum fluorescence emission at less than 490 nm (Matz, 1999): ClavCFP (a.k.a. ClavFP484) from *Clavularia* sp., dsCFP (a.k.a. dsFP483) from *Discosoma striata*, and amCFP (a.k.a. amFP486) from *Anemonia majano*. At least one other CFP, mcCFP (a.k.a. mcCFP477) from *Montastrea cavemosa*, has been recently reported (Sun et al., FEBS Lett., 570:175-83, 2004). One other CFP, asCFP (a.k.a. MiCy) from *Acropara* sp., has a wavelength of maximum fluorescence of 495 nm, and, therefore, is essentially green (as opposed to cyan) in its fluorescence (Karasawa et al., Biochem. J., 381:307-12, 2004). The naturally-occurring CFPs have quantum yields (QY) of 0.24-0.48 and extinction coefficients (EC) of 24,000-40,000M-1 cm-1. All of the naturally-occurring CFPs are oligomers, with some reported to be trimers and some reported to be tetramers. Protein-sequence alignments of ClavCFP, dsFP483, and amFP483 revealed that, of 227 structurally-aligned residues, there are 78 residues that are conserved in all 3 CFPs (FIG. 3). There are an additional 91 residues that are conserved in two of the three CFPs.

Considering only these positions, the inventors determined that ClavCFP is the variant at 19%, dsFP483 at 34%, and amFP486 at 47%, of the 91 positions. Thus, ClavCFP is the closest to a "consensus" sequence. ClavCFP has one cysteine (position 175 with DsRed numbering), while each of dsFP483 and amFP486 has five cysteines. Multiple cysteine residues are undesirable, due to the unpredictable effects of thiol oxidation in applications where the CFP is targeted to an oxidizing subcellular environment—such as the secretary pathway or the bacterial periplasm. Accordingly, the inventors concluded that ClavCFP is a preferred template upon which to base this directed evolution.

Example 3

Library Construction and Mutagenesis

Figure 15:
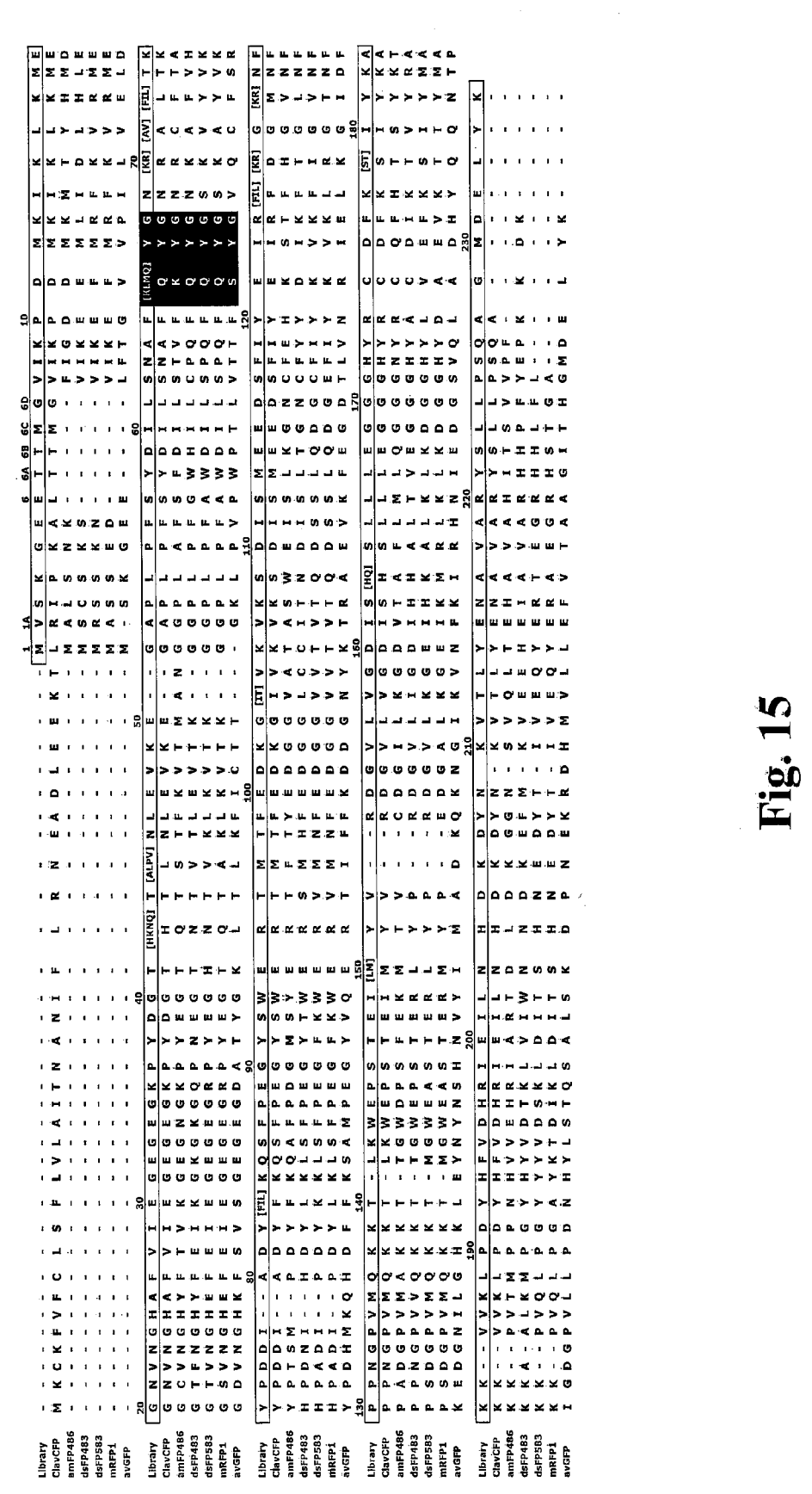
Figure 16:
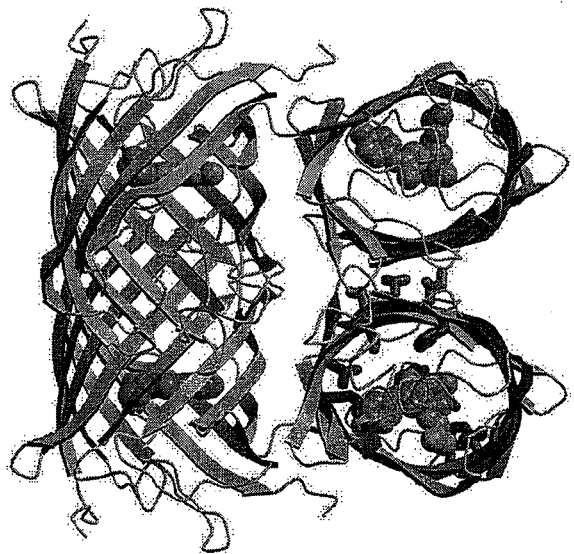
FIG. 16A illustrates degenerate amino acid positions in the synthetic library of FIG. 15, mapped onto the structure of DsRed, PDB ID 1G7K (Yarbrough, 2001). External positions are colored in green, and internal positions are colored in red. Position 66 is part of the chromophore and colored cyan.
FIG. 16B shows residues at which degenerate codons were introduced in the designed library.

The inventors commissioned the synthesis of the gene library encoding the designed protein library from the DNA Technologies Unit at the NRC Plant Biotechnology Group. The important features of the designed gene included: mammalian optimized codon usage, deletion of forty residues from the N-terminus, addition of the seven N-terminal and seven C-terminal residues of avGFP, semi-degenerate codons encoding potential "tetramer-breaking" mutations at three external positions, and semi-degenerate codons encoding potential "rescuing" mutations at eleven internal positions (FIGS. 11, 15, and 16). Library quality was verified by sequencing 77 independent clones, of which nine (12%) were confirmed to contain mutations at only the desired positions.

The initial synthetic gene library was digested with Xho1 and EcoR1 and ligated into similarly digested pBAD/HisB vector (Invitrogen). Subsequent libraries with saturation mutagenesis at a particular residue were constructed by either by an overlap-extension PCR method (Campbell, 2002) or the Quikchange protocol (Stratagene). Randomly mutated libraries were constructed by error-prone PCR as previously described (Campbell, 2002) under conditions optimal for 3 mutations per 1,000 bp (Fromant, 1995). Full-length gene libraries resulting from overlap-extension PCR or error-prone PCR were ligated into the XhoI and EcoR1 restriction sites of pBAD/HisB. Regardless of library assembly method, electrocompetent *Escherichia coli* strain DH10B (Invitrogen) was transformed and plated on Luria-Bertani (LB)/agar plates supplemented with ampicillin (0.1 mg/ml) and L-arabinose (0.02%). Plates were incubated for 14 h at 37° C. prior to screening.

Example 4

Screening

The system for imaging the fluorescence of bacterial colonies grown on 10 cm Petri dish is a custom built device similar to one previously described6. Briefly, the light from a 175W xenon-arc lamp (Sutter) is passed through a 426 nm to 446 nm bandpass filter (Chroma) and into a bifurcated fiber optic bundle (Newport). Light exiting the fiber optic bundle illuminates (0.04 mW/cm2) a 10 cm dish placed in a recessed holder on the bench top. For all screening up to the identification of mTFP0.6, colony fluorescence was screened by viewing illuminated plates through a pair of custom goggles fitted with image quality 3 mm thick GG455 glass (Chroma). When viewed through these goggles, colonies fluorescing at 480-490 nm have a distinctly bluish hue and are easily distinguishable from 'greenish' colonies emitting at 500-510 nm. For the identification of mTFP0.7, colony fluorescence was digitally imaged with a Retiga 1300i 12-bit CCD camera (QImaging) fitted with filter wheel (Sutter) that contains both a 480/40 nm and a 530/30 nm bandpass filter. Through the use of custom macros for Inage Pro Plus (Media Cybernetics), images in both emission channels were acquired and the fluorescence intensities of all colonies were individually integrated. Colonies with high 480/530 nm intensity ratios and high brightness at 480 nm were selected for further characterization.

For the identification of mTFP0.8, mTFP0.9, and mTFP1, the screening protocol was modified in order to select for photostability. We equipped six Royal Blue (peak emission at 455 nm) Luxeon™ V light emitting diodes (LEDs) (Lumileds Lighting) with narrow beam lenses (Fraen) and positioned them to evenly illuminate (55 mW/cm2) the 10 cm dish in the imaging system described above. Through the use of a custom serial port connection, the LEDs could be switched on and off at computer controlled intervals. Through the use of a custom serial port connection, the LEDs could be switched on and off at computer controlled intervals. An Image Pro Plus macro (Media Cybernetics) was used to automate acquisition and processing. For each plate, fluorescence images were acquired following a series of programmed intervals of intense illumination. Using this system, we could identify colonies with decreased propensity to photo-convert or otherwise photo-bleach.

For all screening protocols, colonies with more intense fluorescence or decreased propensity to photo-convert were picked and cultured overnight in 4 ml LB media containing ampicillin and arabinose. The following day 0.1 ml of each culture was dispensed into a 96-well plate (Nunc) and the full emission spectra of each variant measured with a Safire2 plate reader (Tecan). Variants with the most blue-shifted and intense emission peak were used as templates in the subsequent round of library construction.

Example 5

Protein Purification and Characterization

To prepare proteins in sufficient quantity for characterization, E. coli strains DH10B or LMG194 were transformed with the pBAD/His B expression vector containing the gene of interest. A single colony was used to inoculate a 4 ml culture that was allowed to grow overnight (37° C., 225 rpm) before being diluted into 1 L of LB media containing ampicillin (0.1 mg/ml) and arabinose (0.2%). The culture was allowed to grow for 12 h before cells were harvested by centrifugation and lysed by French Press. Proteins were purified by Ni-NTA chromatography (Amersham). Cameleon constructs were further purified by gel filtration chromatography using a HiLoad 16/60 Superdex 75 µg column (GE Healthcare). Proteins were dialyzed into 50 mM Tris, pH 7.5.

The oligomeric structure of mTFP variants was determined by gel filtration chromatography on a HiLoad 16/60 Superdex 75 µg gel filtration column. Samples of the dimeric dTomato and the monomeric mCherry proteins (Shaner, 2004) were expressed and purified as described above and used as size standards. The AKTA basic liquid chromatography system (GE Healthcare) can monitor multiple wavelengths simultaneously. Purified TFP variants were mixed with either dTomato or mCherry and their respective elution profiles monitored separately at 450 nm and 550 nm, respectively.

Example 6

Spectoscopy

Figure 17A:
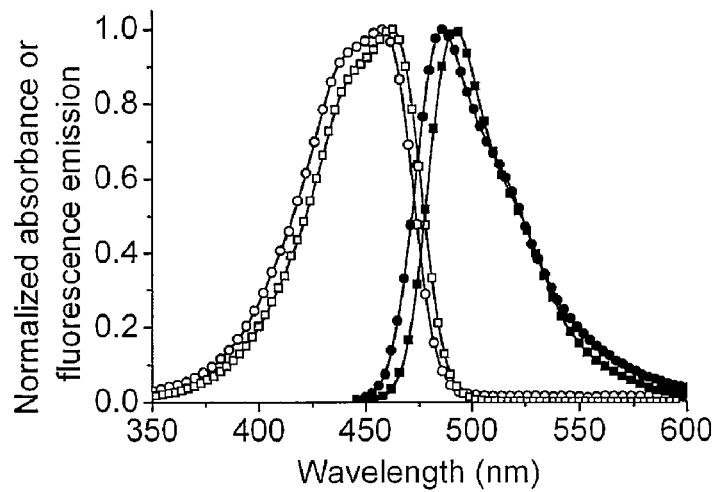
FIG. 17: Absorbance and fluorescence emission spectra of dTFP0.2, mTFP1, and selected fluorescence proteins. (A) Absorbance (open symbols) and fluorescence emission (filled symbols) spectra of dTFP0.2 (○, ●) and mTFP1 (□, ■). (B) Fluorescence emission spectra of mCerulean (○) (Rizzo, 2004 & 2005), mTFP1 (□), EGFP (Δ), Citrine (●) (Griesbeck, 2001), mOrange (■), and mCherry (▲)(Shaner, 2004).
Figure 17B:
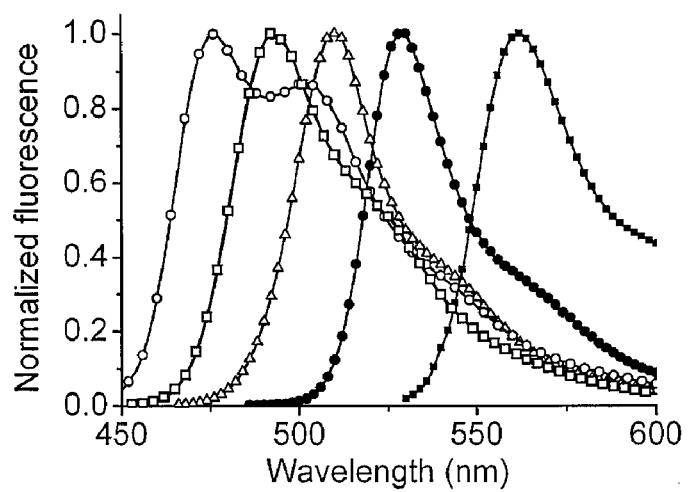

Absorption spectra were recorded on a DU-800 UV-visible spectrophotometer (Beckman). Quantum yields for TFP variants were measured using fluorescein in 10 mM NaOH as the reference standard (Brannon, 1978). Extinction coefficients were measured by the alkali denaturation method (Shaner, 2004; Ward, 1998). A QuantaMaster spectrofluorometer (Photon Technology International) was used to acquire the emission spectra (excitation at 435 nm) shown in FIG. 8 and FIG. 17. All emission spectra have been corrected for the instrument response. Fluorescence lifetimes were determined on a TimeMaster time-resolved spectrofluorometer (Photon Technology International), which uses the stroboscopic optical boxcar technique (James, 1992). Lifetimes were determined in 10 mM Tris pH 8.0 with 1 mM EDTA and 50 mM NaCl at a protein concentration of 0.1 µM. A nitrogen dye laser at 440 nm was used for excitation, and the emission monochromator was set to either 480 nm (for mECFP and mCerulean) or 490 nm for mTFP1. A 480/40 nm bandpass filter was used on the emission channel to further minimize scattered light. Slits were adjusted as necessary to obtain adequate fluorescent intensity when using polarizing filters at 'magic angle' conditions or lower concentrations of fluorescent protein. The photostability of mTFP1 under arc lamp illumination was determined using the method of Shaner et al. (Shaner, 2005).

To determine the pH-dependence of the fluorescence emission of mECFP, mCerulean, and mTFP1, each protein (stock solution of 1 mg/ml in 5 mM Tris pH 7) was diluted 1:100 in a 96-well plate black clear bottom plate (Corning) containing 0.1 ml buffer (100 mM) at pH values ranging from 2 to 9. Full emission spectra at each pH were acquired with a Safire2 plate reader (Tecan). The relative fluorescence at each pH was measured at the peak wavelength.

Example 7

Cameleons and Actin-Fusion for Imaging in Mammalian Cells

To construct expression vectors for cameleon variants, the gene encoding yellow cameleon3.3 (YC3.3) was first inserted into the Xho1 and EcoR1 sites of the pBAD/His B bacterial expression vector (Griesbeck, 2001). The cDNAs encoding mECFP, mCerulean, and mTFP1 were each PCR amplified with primers that added a 5' Xho1 and a 3' Sph1 site. To maintain identical linker lengths, the 3' Sph1 site was appended immediately after the codon encoding Ala227 of mECFP and mCerulean or after the codon encoding the structurally aligned Arg220 of mTFP1. The purified PCR products were digested and ligated into the similarly digested YC3.3 gene. Cameleons expressed in E. Coli were expressed and purified as described herein. To create the mTFP1-YC3.3 mammalian cell expression vector, the full-length gene in pBAD/His B was PCR amplified with a 5' primer that appended a HindIII restriction site, a Kozak sequence (gccaccgccATGc, where ATG is the start codon (SEQ ID NO: 17), and the endoplasmic reticulum (ER) targeting sequence of calreticulin (MLLSVPLLLGLLGLAAAD) (SEQ ID NO: 18). The 3' primer appended the ER retention signal (KDEL) followed by an EcoR1 restriction site. The PCR product was digested with HindIII/EcoR1 and ligated with appropriately digested pcDNA3 (Invitrogen).

To create the mTFP1-actin mammalian expression plasmid, the gene encoding mTFP1 was PCR amplified with a 5' primer encoding an Nhe1 site and a 3' primer encoding an Xho1 site. The purified and digested PCR product was ligated into the pEGFP-actin vector (Clontech) that had been previously digested with the same restriction enzymes to excise the EGFP coding sequence. DNA was purified by Plasmid Midi kit (Qiagen). HeLa cells were cultured in DMEM (Invitrogen) supplemented with 10% FBS (Sigma) at 37° C. Cells in 35 mm imaging dishes were transfected with 4 µg plasmid DNA mixed with 10 µg PEI in 0.5 ml OptiMEM™ (Invitrogen) and serum was added after 3 h. Approximately 14 h later the medium was exchanged for Hanks' Balanced Salt Solution (HBSS) containing no calcium chloride, magnesium chloride, magnesium sulfate, or phenol red (Invitrogen) or PBS and the cells were imaged. HeLa cells expressing mTFP1-β-actin or mTFP1-α-tubulin were imaged using a LSM510 confocal microscope (Zeiss) equipped with a 5 mW 458 nm excitation laser. HeLa cells expressing mTFP1-YC3.3 were imaged with a Zeiss Axiovert 200M epi-fluorescence inverted microscope equipped with a xenon arc lamp and a monochrome Retiga 2000R 12-bit cooled CCD camera (QImaging). The external excitation filter wheel, excitation shutter, and emission filter wheel are controlled through a Lambda 10-3 controller (Sutter). Only dichroic mirrors are housed in the motorized reflector turret. The QED In Vivo software package (Media Cybernetics) is used for automated computer control of all microscope hardware and for quantitative image analysis. To create the mTFP1-α-tubulin expression vector, an identical procedure was used to replace the EGFP gene in pEGFP-tub (Clontech) with the gene encoding mTFP1.

Example 8

Development of the Variants

The sequence of mutations and changes that led to the variants described herein can be summarized as follows:
1. cCFP484: initial wild-type sequence;
2. dTFP0.10: wild-type cCFP484 (a.k.a. TFP) with additional mutations H42N, L44V, L72F, F124L, D125K, M127K, M150L, S179T;
    deleted $1^{st}$ 40 residues, and appended MVSKGEE (SEQ ID NO: 19) to the start (N-terminus) of the protein;
    appended GMDELYK (SEQ ID NO: 20) to the end (C-terminus) of the protein;
3. dTFP0.20: dTFP0.10 with additional mutations D81N, S226P;
4. dTFP0.30: dTFP0.20 with additional mutations Q66G, K182R;
5. tdTFP0.30: genetically fused 2 copies of dTFP0.3, in which GMDELYK (SEQ ID NO: 20) was deleted from the C-terminus of the first copy, and MVSKGEE (SEQ ID NO: 19) was deleted from the N-terminus of the second copy;
    a linker sequence of TGSTLVSGSGTA (SEQ ID NO: 21) was used;
    the S226P mutation was reverted to P in the first copy;
6. mTFP0.3: dTFP0.2 with additional mutations S162K, S164K;
7. mTFP0.4: mTFP0.3 with additional mutations Q66C, C175V;
8. mTFP0.5: mTFP0.4 with additional mutation S62T, C66G, A80P, K127E, K182R, N216S
9. mTFP0.6: mTFP0.4 with additional mutation S2N, G66A, L213V
    replaced residues L223 to A228 (sequence LLPSQA (SEQ ID NO: 22)) with sequence TG;
10. mTFP0.7: mTFP0.6 with additional mutations N2S (reversion), V44I, R123H, Y173H, V186A;
11. mTFP0.8: mTFP0.7 with additional mutation N63T
12. mTFP0.9: mTFP0.8 with additional mutation K142G, E144D, P145A, I149R, L150M (reversion to wild-type sequence), I161V;
13. mTFP1.0: mTFP0.9 with additional mutation L141T, V158K, Y221N, G224D.

Discussed below are results obtained by the inventors in connection with the experiments of Examples 2, 3 and 8:

Results of Directed Evolution

Figure 18:
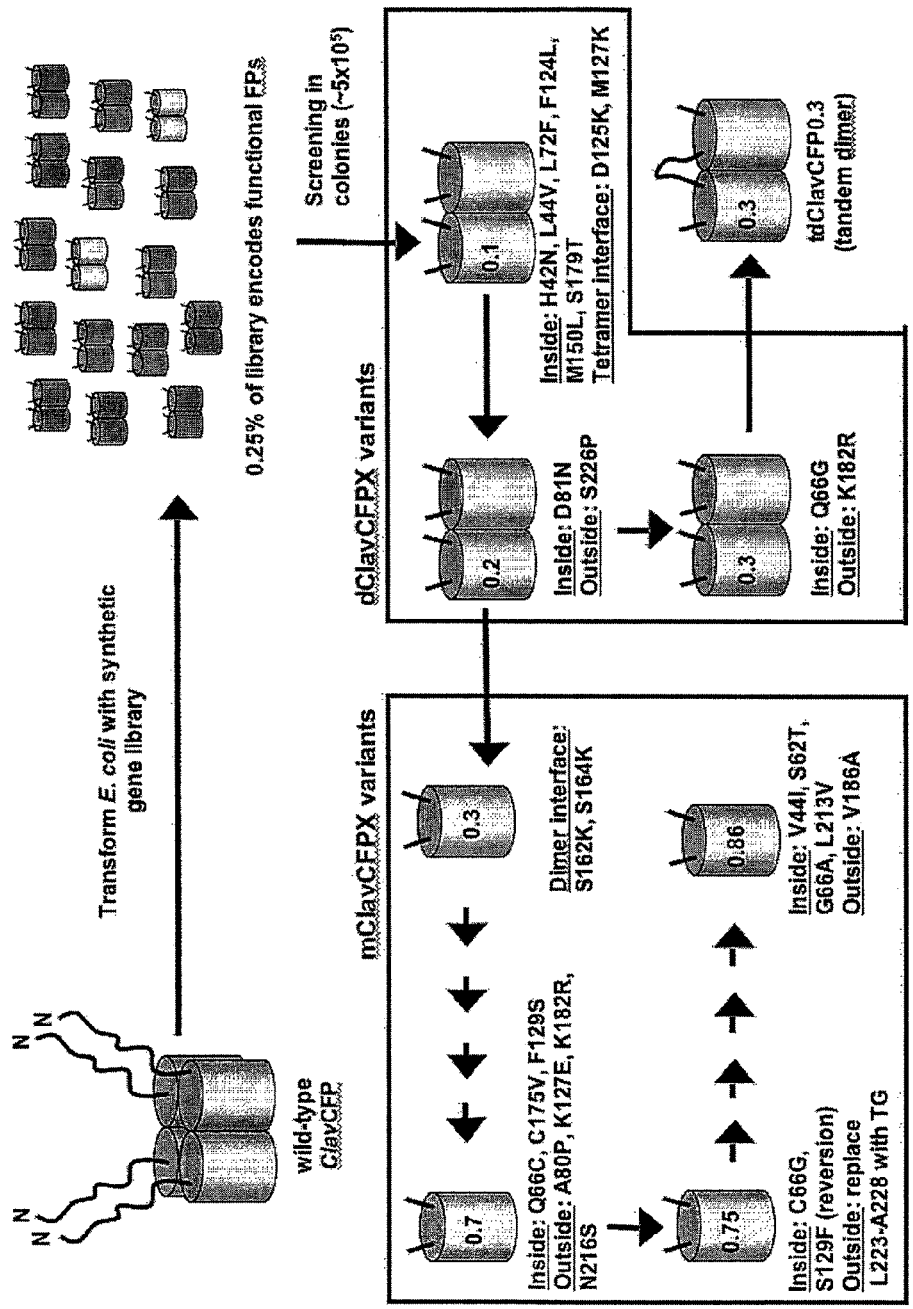
FIG. 18 provides an overview of the library screening and the subsequent directed evolution process. Only 0.25% of the gene library encoded functional fluorescent proteins; of these, approximately 50% were green fluorescent and 50% were cyan fluorescent.
Figure 19:
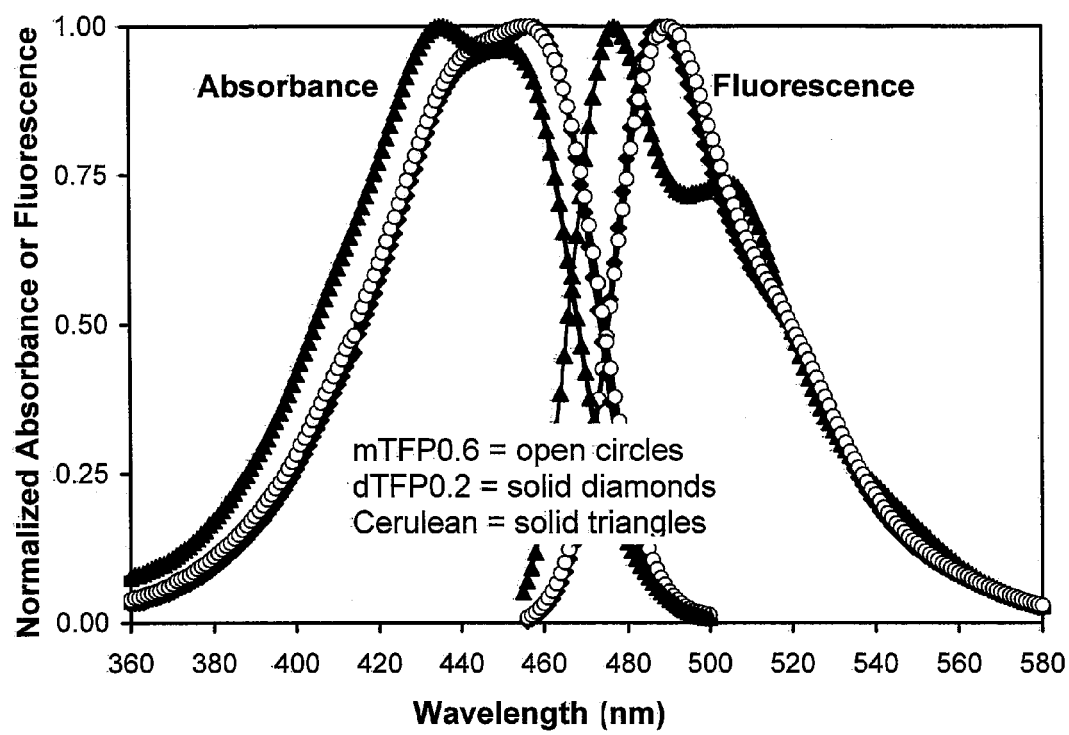
FIG. 19 illustrates fluorescence excitation and emission for Cerulean, dTFP0.2, and mTFP0.7. Note that mTFP0.7 is slightly red-shifted from dTFP0.2, but both proteins have a narrow fluorescence emission compared to Cerulean. The narrow fluorescence emission can be attributed to the different chromophore structure.
Figure 20:
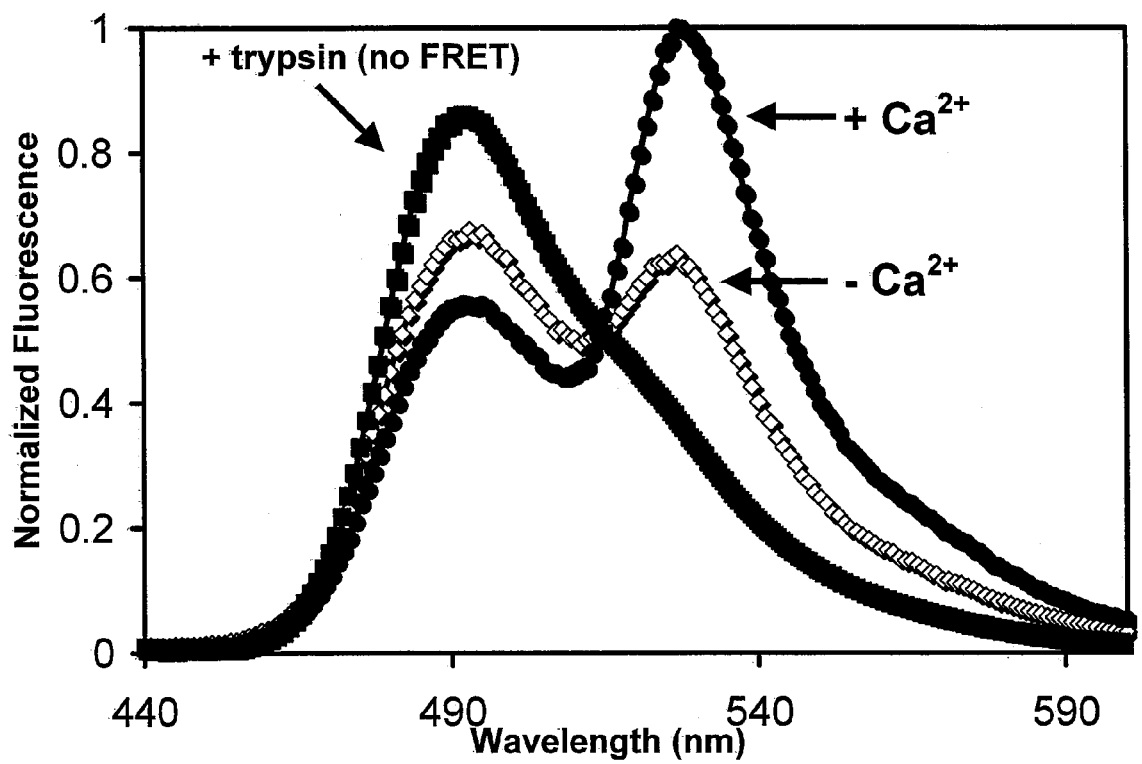
FIG. 20 depicts a demonstration of mTFP0.6 as a Forster (or fluorescence) resonance energy transfer (FRET) donor to Citrine (a YFP) in a ratiometric calcium sensor. The results of this experiment are summarized in Table 5 of the Examples.

Extensive screening of the synthetic gene library resulted in identification of a brightly-fluorescent dimer (quantum yield (QY)=0.73, extinction coefficient (EC)=42,000 M-1 cm-1) with eight mutations relative to the wild-type sequence (FIGS. 18 and 19). Directed evolution was used to evolve the dimer to a substantially-brighter variant (QY=0.89, EC=60,000 M-1 cm-1). Site-directed mutagenesis of the residues in the predicted dimer interface produced a monomeric (QY=0.41, EC=19,000 M-1 cm-1) version that required many rounds of directed evolution in order to rescue and improve the fluorescent brightness. Currently, mTFP0.86 has a QY=0.65 and an EC=59,000 M-1 cm-1; mTFP0.86 is 3.6-fold brighter than avCFP, and 1.4-fold brighter than Cerulean (Rizzo, 2004).

Evaluation of mTFP as a Fret Donor

Analogous versions of yellow cameleon 3.3 (YC3.3), containing either ECFP, Cerulean, or an mTFP-0.6, were constructed, and their response to Ca2+ was determined (Miyawaki et al., Nature, 388:882-87,1997). Cameleon is a Ca2+ reporter that has been optimized to maximize the change in ratio between an ECFP donor and a YFP acceptor. Therefore, it is not surprising that substituting mTFP0.6 for ECFP resulted in a decreased % ratio change. However, the high FRET efficiencies observed with mTFP0.6, in both the presence and absence of Ca2+, showed that it is a very good FRET donor to citrine (FIG. 8 and Table 5).

TABLE 5

Summary of ratio changes and FRET efficiency changes for "cameleon-type" calcium sensors, based on either avCFP, Cerulean, or mTFP0.6.

| | ECFP | | Cerulean | | mTFP0.6 | |
|---|---|---|---|---|---|---|
| | yellow/cyan ratio | FRET efficiency | yellow/cyan ratio | FRET efficiency | yellow/cyan ratio | FRET efficiency |
| $-Ca^{2+}$ | 1.48 | 14% | 1.28 | 13% | 0.94 | 25% |
| $+Ca^{2+}$ | 3.59 | 37% | 2.93 | 35% | 1.79 | 38% |
| % ratio change | 242% | | 230% | | 190% | |
| Δ FRET efficiency | 23% | | 22% | | 13% | |

Outlook

Figure 21:
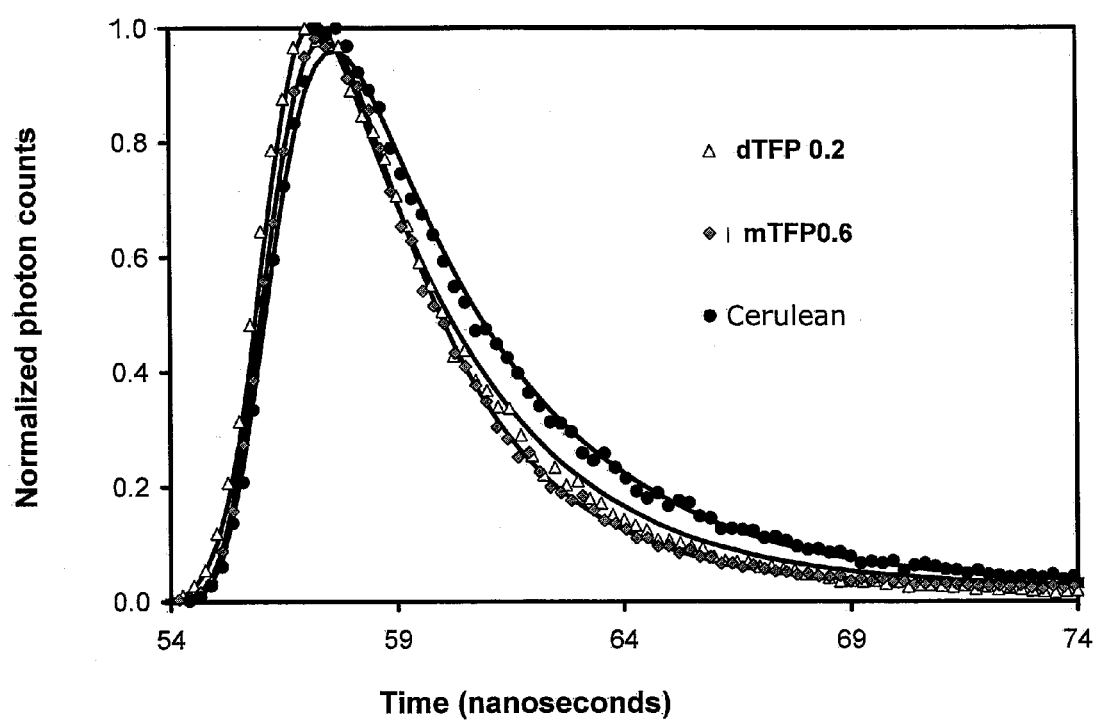
FIG. 21 presents the fluorescence lifetime decay for Cerulean, dTFP0.2, and mTFP0.6.
Figure 22:
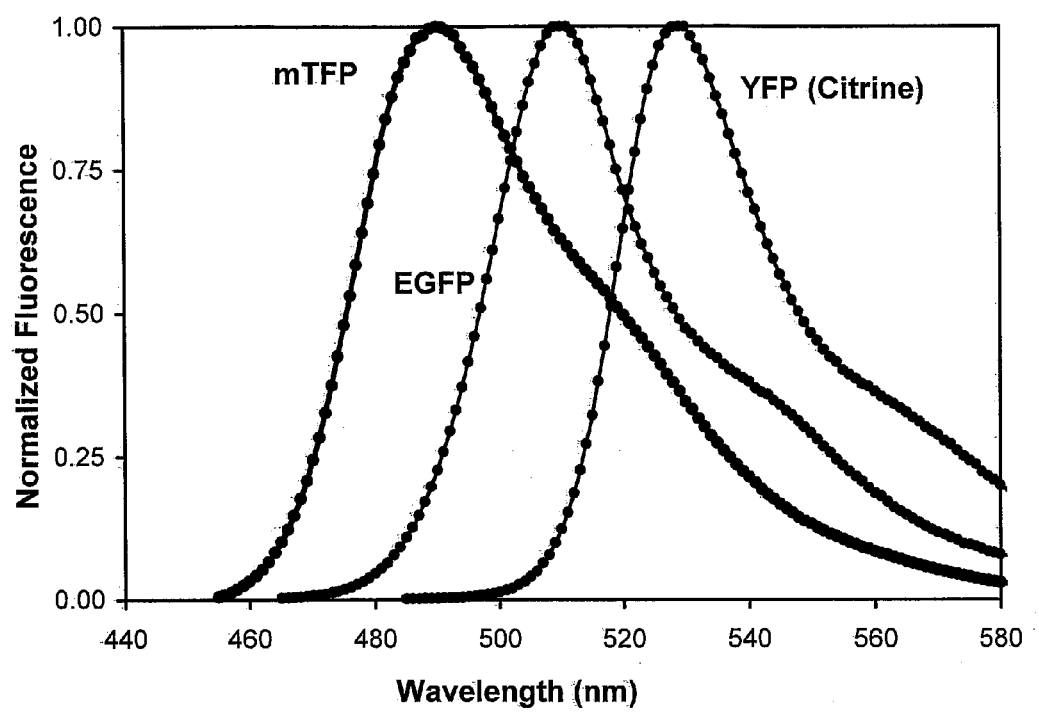
FIG. 22 presents the fluorescent emission spectra of mTFP, avGFP, and Citrine (a YFP).

Both mTFP0.6 (labelled mTFP0.6) and Cerulean can be fitted to a single exponential fluorescence lifetime decay (FIG. 21). The inventors have inserted mTFP0.6 (labelled mTFP0.6) into cameleon-type constructs, and demonstrated that it is an excellent FRET donor to Citrine. It is anticipated that mTFP can be optimized, and that a detailed comparison can be made to ECFP and Cerulean for multicolor imaging, FRET imaging, and FLIM experiments in live cells. mTFP will complement the existing preferred avGFP and YFP variants better than avCFP or Cerulean currently do (FIG. 22).

While the foregoing invention has been described in some detail for purposes of clarity and understanding, it will be appreciated by one skilled in the art, from a reading of the disclosure, that various changes in form and detail can be made without departing from the true scope of the invention in the appended claims.

REFERENCES

The following references are referred to by first author's last name and year of publication, in parenthesis, in the above description and are incorporated herein as if reproduced in their entirety.

Ando, R.; Mizuno, H. and Miyawaki, A. *Science,* 306:1370-73, 2004.
Ausubel et al., eds., *Current Protocols in Molecular Biology* (New York, N.Y.: John Wiley & Sons, Inc., 2001.
Bevis, B. J. and Glick, B. S., *Nat Biotechnol* 20, 83-87 (2002).
Brannon, J. H. and Magde, D., *Journal of Physical Chemistry* 82, 705-709 (1978).
Campbell, R. E.; Tour, O.; Palmer, A. E.; Steinbach, P. A.; Baird, G. S.; Zacharias, D. A. and Tsien, R. Y. *Proc Natl Acad Sci USA* 99, 7877-7882 (2002).
Fromant, M., Blanquet, S. and Plateau, P., *Anal Biochem* 224, 347-353 (1995).
Griesbeck, O., Baird, G. S., Campbell, R. E., Zacharias, D. A. and Tsien, R. Y., *J Biol Chem* 276, 29188-29194 (2001).

Heim, R.; Prasher, D. C. and Tsien, R. Y., *Proc. Nat. Acad. Sci., USA*, 91:12501-504, (1994).

Heim, R., Cubitt, A. B. and Tsien, R. Y., *Nature* 373, 663-664 (1995).

Heim, R. and Tsien; R. Y. *Curr Biol* 6, 178-182 (1996).

International Application Publication No. WO0127150.

James, D. R., Siemiarczuk, A. and Ware, W. R., *Review of Scientific Instruments* 63, 1710-1716 (1992).

Karasawa, S.; Araki, T.; Nagai, T.; Mizuno, H. and Miyawaki, A. *Biochem. J.*, 381:307-12, 2004.

Karasawa, S.; Araki, T.; Yamamoto-Hino, M. and Miyawaki, A. *J. Biol. Chem.*, 278:34167-171, 2003.

Lukyanov, K. A.; Chudakov, D. M.; Lukyanov, S. and Verkhusha, V. V. *Nat Rev Mol Cell Biol*, 6, 885-891 (2005).

Maniatis et al., *Molecular Cloning: A Laboratory Manual*, 2nd ed. (Cold Spring Harbor: Cold Spring Harbor Laboratory, 1989.

Matz, M. V.; Fradkov, A. F.; Labas, Y. A.; Savitsky; A. P.; Zaraisky, A. G.; Markelov, M. L. and Lukyanov, S. A. *Nat Biotechnol* 17, 969-973 (1999).

Matz, M. V.; Fradkov, A. F.; Labas, Y. A.; Savitsky; A. P.; Zaraisky, A. G.; Markelov, M. L. and Lukyanov, S. A. *Nat Biotechnol* 17, 1227 (1999).

Miyawaki, A.; Llopis, J.; Heim, R.; McCaffery, J. M.; Adams, J. A.; Ikura, M. and Tsien, R. Y. *Nature* 388, 882-887 (1997).

Miyawaki, A. and Tsien, R. Y. *Methods Enzymol*, 327, 472-500 (2000).

Nguyen, A. W. and Daugherty, P. S. *Nat Biotechnol* 23, 355-360 (2005).

Ormo, M. et al. *Science* 273, 1392-1395 (1996).

Rizzo, M. A., Springer, G. H., Granada, B. & Piston, D. W. *Nat Biotechnol* 22, 445-449 (2004).

Rizzo, M. A. and Piston, D. W., *Biophys J* 88, L14-16 (2005).

Shaner et al., *Nat. Biotechnol.*, 22:1567-72, 2004.

Shaner, N. C., Steinbach, P. A. and Tsien, R. Y. *Nat Methods* 2, 905-909 (2005).

Shimomura, O. *Febs Letters* 104, 220-222 (1979).

Sun, Y.; Castner, E. W. Jr., Lawson, C. L. Falkowski, P. G. *FEBS Lett.*, 570:175-83, 2004.

Tsien, R. Y., *Annu. Rev. Biochem.*, 67:509-44, 1998.

Ward, W. W. in Green Fluorescent Protein: Properties, Applications, and Protocols. (ed. M. K. Chalfie, S.) 45-75 (Wiley, New York; 1998).

Yang, F., Moss, L. G. & Phillips, G. N., Jr. *Nat Biotechnol* 14, 1246-1251 (1996).

Yarbrough, D.; Wachter, R. M.; Kallio, K.; Matz, M. V. and Remington, S. J.; *Proc. Natl Acad. Sci., USA*, 98:462-67, 2001

Zacharias, D. A., Violin, J. D., Newton, A. C. & Tsien, R. Y., *Science* 296, 913-916 (2002).

Zhang, J.; Campbell, R. E.; Ting, A. Y. and Tsien, R. Y., *Nat. Rev. Mol. Cell Biol.*, 3:906-18, 2002.

---

What is claimed is:

1. An isolated nucleic acid encoding the amino acid sequence of SEQ ID NO: 7.

2. The isolated nucleic acid of claim 1, wherein the nucleic acid comprises the nucleotide sequence of SEQ ID NO: 6.

3. The isolated nucleic acid of claim 1 which is compatible with mammalian codon usage.

4. The isolated nucleic acid of claim 3, which is compatible with human codon usage.

5. The isolated nucleic acid of claim 1, wherein the encoded polypeptide has a chromophore capable of fluorescence with an excitation maximum ranging from 450 to 460 nm and an emission maximum ranging from 485 to 495 nm.

6. The isolated nucleic acid of claim 1, wherein the encoded polypeptide is monomeric.

7. A vector comprising the nucleic acid of any one of claims 1, 2, 3, 4, 5 and 6.

8. The vector of claim 7, which is a plasmid.

9. The vector of claim 7, wherein the nucleic acid is cDNA.

10. An isolated host cell comprising the vector of claim 7.

* * * * *

SEQUENCE LISTING

```
<160> NUMBER OF SEQ ID NOS: 22

<210> SEQ ID NO 1
<211> LENGTH: 760
<212> TYPE: DNA
<213> ORGANISM: Artificial
<220> FEATURE:
<223> OTHER INFORMATION: DNA sequence of the synthetic gene library

<400> SEQUENCE: 1
agcaggtcta gactcgagca tggtgagcaa gggcgaggag accacaatgg gcgtaatcaa      60
gcccgacatg aagatcaagc tgaagatgga gggcaacgtg aacggccacg ccttcgtgat     120
cgagggcgag ggcgagggca agccctacga cggcaccmas accsycaacc tggaggtgaa     180
ggagggagcc cccctgccct tctcctacga catcctgtcc aacgccttcm wgtacggcaa     240
carggychtc accaagtacc ccgacgacat cgccgactac htcaagcagt ccttccccga     300
gggctactcc tgggagcgca ccatgaccct cgaggacaag ggcaycgtga aggtgaagtc     360
cgacatctcc atggaggagg actccttcat ctacgagatc cgchtcargg gcargaactt     420 ccccccaac ggccccgtga tgcagaagaa gaccctgaag tgggagccct ccaccgagat     480
cmtgtacgtg cgcgacggcg tgctggtggg cgacatctcc castccctgc tgctggaggg     540
cggcggccac taccgctgcg acttcaagwc catctacaag gccaagaagg tggtgaagct     600
gcccgactac cacttcgtgg accaccgcat cgagatcctg aaccacgaca aggactacaa     660
caaggtgacc ctgtacgaga acgccgtggc ccgctactcc ctgctgccct cccaggcagg     720
catggacgag ctgtacaagt aagaattcgg atcctgcgta                            760

<210> SEQ ID NO 2
<211> LENGTH: 708
<212> TYPE: DNA
```

<210> SEQ ID NO 2
<211> LENGTH: 708
<212> TYPE: DNA
<213> ORGANISM: Artificial
<220> FEATURE:
<223> OTHER INFORMATION: Complete DNA sequence of mTFP0.86

<400> SEQUENCE: 2

```
atggtgagca agggcgagga gaccacaatg ggcgtaatca agcccgacat gaagatcaag      60
ctgaagatgg agggcaacgt gaatggccac gccttcgtga tcgagggcga gggcgagggc     120
aagccctacg acggcaccaa caccatcaac ctggaggtga aggagggagc ccccctgccc     180
ttctcctacg acattctgac caacgccttc gcttacggca cagggcctt caccaagtac     240
cccgacgaca tccccaacta cttcaagcag tccttccccg agggctactc ttgggagcgc     300
accatgacct tcgaggacaa gggcatcgtg aaggtgaagt ccgacatctc catggaggag     360
gactccttca tctacgagat acgcctcaag ggcgagaact cccccccaa cggccccgtg     420
atgcagaaga agaccctgaa gtgggagccc tccaccgaga tcctgtacgt gcgcgacggc     480
gtgctggtgg gcgacatcaa gcacaagctg ctgctggagg gcggcggcca ctaccgcgtt     540
gacttcaaga ccatctacag ggccaagaag gcggtgaagc tgcccgacta ccacttcgtg     600
gaccaccgca tcgagatcct gaaccacgac aaggactaca caaggtgac cgtttacgag     660
agcgccgtgg cccgctactc caccggcggc atggacgagc tgtacaag               708
```

<210> SEQ ID NO 3
<211> LENGTH: 236
<212> TYPE: PRT
<213> ORGANISM: Artificial
<220> FEATURE:
<223> OTHER INFORMATION: Complete protein sequence of mTFP0.86

<400> SEQUENCE: 3

```
Met Val Ser Lys Gly Glu Glu Thr Thr Met Gly Val Ile Lys Pro Asp
1               5                   10                  15

Met Lys Ile Lys Leu Lys Met Glu Gly Asn Val Asn Gly His Ala Phe
            20                  25                  30

Val Ile Glu Gly Glu Gly Glu Gly Lys Pro Tyr Asp Gly Thr Asn Thr
        35                  40                  45

Ile Asn Leu Glu Val Lys Glu Gly Ala Pro Leu Pro Phe Ser Tyr Asp
    50                  55                  60

Ile Leu Thr Asn Ala Phe Ala Tyr Gly Asn Arg Ala Phe Thr Lys Tyr
65                  70                  75                  80

Pro Asp Asp Ile Pro Asn Tyr Phe Lys Gln Ser Phe Pro Glu Gly Tyr
                85                  90                  95

Ser Trp Glu Arg Thr Met Thr Phe Glu Asp Lys Gly Ile Val Lys Val
            100                 105                 110

Lys Ser Asp Ile Ser Met Glu Glu Asp Ser Phe Ile Tyr Glu Ile Arg
        115                 120                 125

Leu Lys Gly Glu Asn Phe Pro Pro Asn Gly Pro Val Met Gln Lys Lys
    130                 135                 140

Thr Leu Lys Trp Glu Pro Ser Thr Glu Ile Leu Tyr Val Arg Asp Gly
145                 150                 155                 160

Val Leu Val Gly Asp Ile Lys His Lys Leu Leu Leu Glu Gly Gly Gly
                165                 170                 175

His Tyr Arg Val Asp Phe Lys Thr Ile Tyr Arg Ala Lys Lys Ala Val
            180                 185                 190

Lys Leu Pro Asp Tyr His Phe Val Asp His Arg Ile Glu Ile Leu Asn
        195                 200                 205
```

His Asp Lys Asp Tyr Asn Lys Val Thr Val Tyr Glu Ser Ala Val Ala
    210                 215                 220

Arg Tyr Ser Thr Gly Gly Met Asp Glu Leu Tyr Lys
225                 230                 235

<210> SEQ ID NO 4
<211> LENGTH: 1434
<212> TYPE: DNA
<213> ORGANISM: Artificial
<220> FEATURE:
<223> OTHER INFORMATION: Complete DNA sequence of a tandem dimer of TFP,
      abbreviated tdTFP0.3

<400> SEQUENCE: 4

| | | | | | |
|---|---|---|---|---|---|
| atggtgagca | agggcgagga | gaccacaatg | ggcgtaatca | agcccgacat | gaagatcaag | 60 |
| ctgaagatgg | agggcaacgt | gaatggccac | gccttcgtga | tcgagggcga | gggcgagggc | 120 |
| aagccctacg | acggcaccaa | caccgtcaac | ctggaggtga | aggagggagc | cccctgccc | 180 |
| ttctcctacg | acattctgtc | caacgccttc | gggtacggca | cagggcctt | caccaagtac | 240 |
| cccgacgaca | tcgccaacta | cttcaagcag | tccttccccg | agggctactc | ctggagcgc | 300 |
| accatgacct | tcgaggacaa | gggcatcgtg | aaggtgaagt | ccgacatctc | catggaggag | 360 |
| gactccttca | tctacgagat | ccgcctcaag | ggcaagaact | tcccccccaa | cggccccgtg | 420 |
| atgcagaaga | agaccctgaa | gtgggagccc | tccaccgaga | tcctgtacgt | cgcgacggc | 480 |
| gtgctggtgg | cgacatctc | ccactccctg | ctgctggagg | gcggcggcca | ctaccgctgc | 540 |
| gacttcaaga | ccatctacag | ggccaagaag | gtggtgaagc | tgcccgacta | ccacttcgtg | 600 |
| gaccaccgca | tcgagatcct | gaaccacgac | aaggactaca | acaaggtgac | cctgtacgag | 660 |
| aacgccgtgg | cccgctactc | cctgctgccc | tcccaggcaa | ccggcagcac | tctagtcagc | 720 |
| ggctccggca | ccgccaccac | aatgggcgta | atcaagcccg | acatgaagat | caagctgaag | 780 |
| atggagggca | acgtgaatgg | ccacgccttc | gtgatcgagg | gcgagggcga | gggcaagccc | 840 |
| tacgacggca | ccaacaccgt | caacctggag | gtgaaggagg | gagccccct | gccttctcc | 900 |
| tacgacattc | tgtccaacgc | cttcgggtac | ggcaacaggg | ccttcaccaa | gtaccccgac | 960 |
| gacatcgcca | actacttcaa | gcagtccttc | cccgagggct | actcctggga | gcgcaccatg | 1020 |
| accttcgagg | acaagggcat | cgtgaaggtg | aagtccgaca | tctccatgga | ggaggactcc | 1080 |
| ttcatctacg | agatccgcct | caagggcaag | aacttccccc | ccaacggccc | cgtgatgcag | 1140 |
| aagaagaccc | tgaagtggga | gccctccacc | gagatcctgt | acgtcgcgca | cggcgtgctg | 1200 |
| gtgggcgaca | tctcccactc | cctgctgctg | gagggcggcg | gccactaccg | ctgcgacttc | 1260 |
| aagaccatct | acagggccaa | gaaggtggtg | aagctgcccg | actaccactt | cgtggaccac | 1320 |
| cgcatcgaga | tcctgaacca | cgacaaggac | tacaacaagg | tgaccctgta | cgagaacgcc | 1380 |
| gtggcccgct | actccctgct | gcccccccag | gcaggcatgg | acgagctgta | caag | 1434 |

<210> SEQ ID NO 5
<211> LENGTH: 478
<212> TYPE: PRT
<213> ORGANISM: Artificial
<220> FEATURE:
<223> OTHER INFORMATION: Complete protein sequence of tdTFP0.3

<400> SEQUENCE: 5

Met Val Ser Lys Gly Glu Glu Thr Thr Met Gly Val Ile Lys Pro Asp
1               5                   10                  15

Met Lys Ile Lys Leu Lys Met Glu Gly Asn Val Asn Gly His Ala Phe

-continued

```
                20                  25                  30
Val Ile Glu Gly Glu Gly Glu Gly Lys Pro Tyr Asp Gly Thr Asn Thr
                35                  40                  45
Val Asn Leu Glu Val Lys Glu Gly Ala Pro Leu Pro Phe Ser Tyr Asp
    50                  55                  60
Ile Leu Ser Asn Ala Phe Gly Tyr Gly Asn Arg Ala Phe Thr Lys Tyr
65                  70                  75                  80
Pro Asp Asp Ile Ala Asn Tyr Phe Lys Gln Ser Phe Pro Glu Gly Tyr
                85                  90                  95
Ser Trp Glu Arg Thr Met Thr Phe Glu Asp Lys Gly Ile Val Lys Val
                100                 105                 110
Lys Ser Asp Ile Ser Met Glu Glu Asp Ser Phe Ile Tyr Glu Ile Arg
            115                 120                 125
Leu Lys Gly Lys Asn Phe Pro Pro Asn Gly Pro Val Met Gln Lys Lys
            130                 135                 140
Thr Leu Lys Trp Glu Pro Ser Thr Glu Ile Leu Tyr Val Arg Asp Gly
145                 150                 155                 160
Val Leu Val Gly Asp Ile Ser His Ser Leu Leu Leu Glu Gly Gly Gly
                165                 170                 175
His Tyr Arg Cys Asp Phe Lys Thr Ile Tyr Arg Ala Lys Lys Val Val
                180                 185                 190
Lys Leu Pro Asp Tyr His Phe Val Asp His Arg Ile Glu Ile Leu Asn
            195                 200                 205
His Asp Lys Asp Tyr Asn Lys Val Thr Leu Tyr Glu Asn Ala Val Ala
210                 215                 220
Arg Tyr Ser Leu Leu Pro Ser Gln Ala Thr Gly Ser Thr Leu Val Ser
225                 230                 235                 240
Gly Ser Gly Thr Ala Thr Thr Met Gly Val Ile Lys Pro Asp Met Lys
                245                 250                 255
Ile Lys Leu Lys Met Glu Gly Asn Val Asn Gly His Ala Phe Val Ile
                260                 265                 270
Glu Gly Glu Gly Glu Gly Lys Pro Tyr Asp Gly Thr Asn Thr Val Asn
            275                 280                 285
Leu Glu Val Lys Glu Gly Ala Pro Leu Pro Phe Ser Tyr Asp Ile Leu
290                 295                 300
Ser Asn Ala Phe Gly Tyr Gly Asn Arg Ala Phe Thr Lys Tyr Pro Asp
305                 310                 315                 320
Asp Ile Ala Asn Tyr Phe Lys Gln Ser Phe Pro Glu Gly Tyr Ser Trp
                325                 330                 335
Glu Arg Thr Met Thr Phe Glu Asp Lys Gly Ile Val Lys Val Lys Ser
                340                 345                 350
Asp Ile Ser Met Glu Glu Asp Ser Phe Ile Tyr Glu Ile Arg Leu Lys
            355                 360                 365
Gly Lys Asn Phe Pro Pro Asn Gly Pro Val Met Gln Lys Lys Thr Leu
            370                 375                 380
Lys Trp Glu Pro Ser Thr Glu Ile Leu Tyr Val Arg Asp Gly Val Leu
385                 390                 395                 400
Val Gly Asp Ile Ser His Ser Leu Leu Leu Glu Gly Gly Gly His Tyr
                405                 410                 415
Arg Cys Asp Phe Lys Thr Ile Tyr Arg Ala Lys Lys Val Val Lys Leu
                420                 425                 430
Pro Asp Tyr His Phe Val Asp His Arg Ile Glu Ile Leu Asn His Asp
            435                 440                 445
```

```
Lys Asp Tyr Asn Lys Val Thr Leu Tyr Glu Asn Ala Val Ala Arg Tyr
    450                 455                 460

Ser Leu Leu Pro Pro Gln Ala Gly Met Asp Glu Leu Tyr Lys
465                 470                 475

<210> SEQ ID NO 6
<211> LENGTH: 711
<212> TYPE: DNA
<213> ORGANISM: Artificial
<220> FEATURE:
<223> OTHER INFORMATION: Complete DNA sequence of mTFP1 (SEQ ID NO: 6)

<400> SEQUENCE: 6
atggtgagca agggcgagga gaccacaatg ggcgtaatca agcccgacat gaagatcaag     60
ctgaagatgg agggcaacgt gaatggccac gccttcgtga tcgagggcga gggcgagggc    120
aagccctacg acggcaccaa caccatcaac ctggaggtga aggagggagc cccccctgccc   180 ttctcctacg acattctgac caccgcgttc gcctacggca cagggccttt caccaagtac    240
cccgacgaca tccccaacta cttcaagcag tccttccccg agggctactc ttggagcgc    300 accatgacct tcgaggacaa gggcatcgtg aaggtgaagt ccgacatctc catggaggag    360
gactccttca tctacgagat acacctcaag ggcgagaact ccccccccaa cggccccgtg    420
atgcagaaga agaccaccgg ctgggacgcc tccaccgaga ggatgtacgt gcgcgacggc    480
gtgctgaagg gcgacgtcaa gcacaagctg ctgctggagg gcggcggcca ccaccgcgtt    540
gacttcaaga ccatctacag ggccaagaag gcggtgaagc tgcccgacta tcactttgtg    600
gaccaccgca tcgagatcct gaaccacgac aaggactaca acaaggtgac cgtttacgag    660
agcgccgtgg cccgcaactc caccgacggc atggacgagc tgtacaagta a            711

<210> SEQ ID NO 7
<211> LENGTH: 236
<212> TYPE: PRT
<213> ORGANISM: Artificial
<220> FEATURE:
<223> OTHER INFORMATION: Complete protein sequence of mTFP1 (SEQ ID NO:
      7)

<400> SEQUENCE: 7

Met Val Ser Lys Gly Glu Glu Thr Thr Met Gly Val Ile Lys Pro Asp
1               5                   10                  15

Met Lys Ile Lys Leu Lys Met Glu Gly Asn Val Asn Gly His Ala Phe
            20                  25                  30

Val Ile Glu Gly Glu Gly Glu Gly Lys Pro Tyr Asp Gly Thr Asn Thr
        35                  40                  45

Ile Asn Leu Glu Val Lys Glu Gly Ala Pro Leu Pro Phe Ser Tyr Asp
    50                  55                  60

Ile Leu Thr Thr Ala Phe Ala Tyr Gly Asn Arg Ala Phe Thr Lys Tyr
65                  70                  75                  80

Pro Asp Asp Ile Pro Asn Tyr Phe Lys Gln Ser Phe Pro Glu Gly Tyr
                85                  90                  95

Ser Trp Glu Arg Thr Met Thr Phe Glu Asp Lys Gly Ile Val Lys Val
            100                 105                 110

Lys Ser Asp Ile Ser Met Glu Glu Asp Ser Phe Ile Tyr Glu Ile His
        115                 120                 125

Leu Lys Gly Glu Asn Phe Pro Pro Asn Gly Pro Val Met Gln Lys Lys
    130                 135                 140
```

```
Thr Thr Gly Trp Asp Ala Ser Thr Glu Arg Met Tyr Val Arg Asp Gly
145                 150                 155                 160

Val Leu Lys Gly Asp Val Lys His Lys Leu Leu Glu Gly Gly Gly
            165                 170                 175

His His Arg Val Asp Phe Lys Thr Ile Tyr Arg Ala Lys Lys Ala Val
            180                 185                 190

Lys Leu Pro Asp Tyr His Phe Val Asp His Arg Ile Glu Ile Leu Asn
            195                 200                 205

His Asp Lys Asp Tyr Asn Lys Val Thr Val Tyr Glu Ser Ala Val Ala
        210                 215                 220

Arg Asn Ser Thr Asp Gly Met Asp Glu Leu Tyr Lys
225                 230                 235
```

<210> SEQ ID NO 8
<211> LENGTH: 240
<212> TYPE: PRT
<213> ORGANISM: Artificial
<220> FEATURE:
<223> OTHER INFORMATION: Complete protein sequence of the synthetic gene
      library (Figure 3)
<220> FEATURE:
<221> NAME/KEY: misc_feature
<222> LOCATION: (47)..(47)
<223> OTHER INFORMATION: "Xaa" is H, N, Q or K
<220> FEATURE:
<221> NAME/KEY: misc_feature
<222> LOCATION: (49)..(49)
<223> OTHER INFORMATION: "Xaa" is L, V, A or P
<220> FEATURE:
<221> NAME/KEY: misc_feature
<222> LOCATION: (71)..(71)
<223> OTHER INFORMATION: "Xaa" is Q, K, M, or L
<220> FEATURE:
<221> NAME/KEY: misc_feature
<222> LOCATION: (75)..(75)
<223> OTHER INFORMATION: "Xaa" is K or R
<220> FEATURE:
<221> NAME/KEY: misc_feature
<222> LOCATION: (76)..(76)
<223> OTHER INFORMATION: "Xaa" is A or V
<220> FEATURE:
<221> NAME/KEY: misc_feature
<222> LOCATION: (77)..(77)
<223> OTHER INFORMATION: "Xaa" is L, F or I
<220> FEATURE:
<221> NAME/KEY: misc_feature
<222> LOCATION: (88)..(88)
<223> OTHER INFORMATION: "Xaa" is L, F or I
<220> FEATURE:
<221> NAME/KEY: misc_feature
<222> LOCATION: (109)..(109)
<223> OTHER INFORMATION: "Xaa" is I or T
<220> FEATURE:
<221> NAME/KEY: misc_feature
<222> LOCATION: (129)..(129)
<223> OTHER INFORMATION: "Xaa" is L, F or I
<220> FEATURE:
<221> NAME/KEY: misc_feature
<222> LOCATION: (130)..(130)
<223> OTHER INFORMATION: "Xaa" is K or R
<220> FEATURE:
<221> NAME/KEY: misc_feature
<222> LOCATION: (132)..(132)
<223> OTHER INFORMATION: "Xaa" is K or R
<220> FEATURE:
<221> NAME/KEY: misc_feature
<222> LOCATION: (155)..(155)
<223> OTHER INFORMATION: "Xaa" is M or L
<220> FEATURE:
<221> NAME/KEY: misc_feature
<222> LOCATION: (168)..(168)
<223> OTHER INFORMATION: "Xaa" is H or Q
<220> FEATURE:

<221> NAME/KEY: misc_feature
<222> LOCATION: (184)..(184)
<223> OTHER INFORMATION: "Xaa" is S or T

<400> SEQUENCE: 8

```
Met Val Ser Lys Gly Glu Glu Thr Thr Met Gly Val Ile Lys Pro Asp
1               5                   10                  15

Met Lys Ile Lys Leu Lys Met Glu Gly Asn Val Asn Gly His Ala Phe
            20                  25                  30

Val Ile Glu Gly Glu Gly Glu Gly Lys Pro Tyr Asp Gly Thr Xaa Thr
        35                  40                  45

Xaa Asn Leu Glu Val Lys Glu Gly Ala Pro Leu Pro Phe Ser Tyr Asp
    50                  55                  60

Ile Leu Ser Asn Ala Phe Xaa Tyr Gly Asn Xaa Xaa Xaa Thr Lys Tyr
65                  70                  75                  80

Pro Asp Asp Ile Ala Asp Tyr Xaa Lys Gln Ser Phe Pro Gly Tyr
                85                  90                  95

Ser Trp Glu Arg Thr Met Thr Phe Glu Asp Lys Gly Xaa Val Lys Val
            100                 105                 110

Lys Ser Asp Ile Ser Met Glu Glu Asp Ser Phe Ile Tyr Glu Ile Arg
            115                 120                 125

Xaa Xaa Gly Xaa Asn Phe Pro Pro Asn Gly Pro Val Met Gln Lys Lys
130                 135                 140

Thr Leu Lys Trp Glu Pro Ser Thr Glu Ile Xaa Tyr Val Arg Asp Gly
145                 150                 155                 160

Val Leu Val Gly Asp Ile Ser Xaa Ser Leu Leu Leu Glu Gly Gly Gly
                165                 170                 175

His Tyr Arg Cys Asp Phe Lys Xaa Ile Tyr Lys Ala Lys Lys Val Val
            180                 185                 190

Lys Leu Pro Asp Tyr His Phe Val Asp His Arg Ile Glu Ile Leu Asn
            195                 200                 205

His Asp Lys Asp Tyr Asn Lys Val Thr Leu Tyr Glu Asn Ala Val Ala
    210                 215                 220

Arg Tyr Ser Leu Leu Pro Ser Gln Ala Gly Met Asp Glu Leu Tyr Lys
225                 230                 235                 240
```

<210> SEQ ID NO 9
<211> LENGTH: 266
<212> TYPE: PRT
<213> ORGANISM: Clavularia sp.
<220> FEATURE:
<223> OTHER INFORMATION: Complete protein sequence of cFP484 (Figure 3)
<300> PUBLICATION INFORMATION:
<301> AUTHORS: Matz,M.V., Fradkov,A.F., Labas,Y.A., Savitsky,A.P.,
      Zaraisky,A.G., Markelov,M.L. and Lukyanov,S.A.
<302> TITLE: Fluorescent proteins from nonbioluminescent Anthozoa
      species
<303> JOURNAL: Nat. Biotechnol.
<304> VOLUME: 17
<305> ISSUE: 10
<306> PAGES: 969-973
<307> DATE: 1999
<308> DATABASE ACCESSION NUMBER: AAF03374
<309> DATABASE ENTRY DATE: 2004-02-17
<313> RELEVANT RESIDUES IN SEQ ID NO: (1)..(266)

<400> SEQUENCE: 9

```
Met Lys Cys Lys Phe Val Phe Cys Leu Ser Phe Leu Val Leu Ala Ile
1               5                   10                  15

Thr Asn Ala Asn Ile Phe Leu Arg Asn Glu Ala Asp Leu Glu Glu Lys
            20                  25                  30
```

```
Thr Leu Arg Ile Pro Lys Ala Leu Thr Thr Met Gly Val Ile Lys Pro
            35                  40                  45

Asp Met Lys Ile Lys Leu Lys Met Glu Gly Asn Val Asn Gly His Ala
 50                  55                  60

Phe Val Ile Glu Gly Glu Gly Lys Pro Tyr Asp Gly Thr His
 65                  70                  75                  80

Thr Leu Asn Leu Glu Val Lys Glu Gly Ala Pro Leu Pro Phe Ser Tyr
                    85                  90                  95

Asp Ile Leu Ser Asn Ala Phe Gln Tyr Gly Asn Arg Ala Leu Thr Lys
                100                 105                 110

Tyr Pro Asp Asp Ile Ala Asp Tyr Phe Lys Gln Ser Phe Pro Glu Gly
            115                 120                 125

Tyr Ser Trp Glu Arg Thr Met Thr Phe Glu Asp Lys Gly Ile Val Lys
        130                 135                 140

Val Lys Ser Asp Ile Ser Met Glu Glu Asp Ser Phe Ile Tyr Glu Ile
145                 150                 155                 160

Arg Phe Asp Gly Met Asn Phe Pro Pro Asn Gly Pro Val Met Gln Lys
                165                 170                 175

Lys Thr Leu Lys Trp Glu Pro Ser Thr Glu Ile Met Tyr Val Arg Asp
            180                 185                 190

Gly Val Leu Val Gly Asp Ile Ser His Ser Leu Leu Leu Glu Gly Gly
        195                 200                 205

Gly His Tyr Arg Cys Asp Phe Lys Ser Ile Tyr Lys Ala Lys Lys Val
    210                 215                 220

Val Lys Leu Pro Asp Tyr His Phe Val Asp His Arg Ile Glu Ile Leu
225                 230                 235                 240

Asn His Asp Lys Asp Tyr Asn Lys Val Thr Leu Tyr Glu Asn Ala Val
                245                 250                 255

Ala Arg Tyr Ser Leu Leu Pro Ser Gln Ala
            260                 265

<210> SEQ ID NO 10
<211> LENGTH: 232
<212> TYPE: PRT
<213> ORGANISM: Discosoma striata
<220> FEATURE:
<223> OTHER INFORMATION: Complete protein sequence of dsFP483 (Figure 3)
<300> PUBLICATION INFORMATION:
<301> AUTHORS: Matz,M.V., Fradkov,A.F., Labas,Y.A., Savitsky,A.P.,
      Zaraisky,A.G., Markelov,M.L. and Lukyanov,S.A.
<302> TITLE: Fluorescent proteins from nonbioluminescent Anthozoa
       species
<303> JOURNAL: Nat. Biotechnol.
<304> VOLUME: 17
<305> ISSUE: 10
<306> PAGES: 969-973
<307> DATE: 1999
<308> DATABASE ACCESSION NUMBER: AAF03370
<309> DATABASE ENTRY DATE: 2001-07-27
<313> RELEVANT RESIDUES IN SEQ ID NO: (1)..(232)

<400> SEQUENCE: 10

Met Ser Cys Ser Lys Ser Val Ile Lys Glu Glu Met Leu Ile Asp Leu
 1               5                  10                  15

His Leu Glu Gly Thr Phe Asn Gly His Tyr Phe Glu Ile Lys Gly Lys
                20                  25                  30

Gly Lys Gly Gln Pro Asn Glu Gly Thr Asn Thr Val Thr Leu Glu Val
            35                  40                  45

Thr Lys Gly Gly Pro Leu Pro Phe Gly Trp His Ile Leu Cys Pro Gln
```

```
                        50                  55                  60
Phe Gln Tyr Gly Asn Lys Ala Phe Val His His Pro Asp Asn Ile His
 65                  70                  75                  80

Asp Tyr Leu Lys Leu Ser Phe Pro Glu Gly Tyr Thr Trp Glu Arg Ser
                 85                  90                  95

Met His Phe Glu Asp Gly Gly Leu Cys Cys Ile Thr Asn Asp Ile Ser
                100                 105                 110

Leu Thr Gly Asn Cys Phe Tyr Tyr Asp Ile Lys Phe Thr Gly Leu Asn
                115                 120                 125

Phe Pro Pro Asn Gly Pro Val Val Gln Lys Lys Thr Thr Gly Trp Glu
            130                 135                 140

Pro Ser Thr Glu Arg Leu Tyr Pro Arg Asp Gly Val Leu Ile Gly Asp
145                 150                 155                 160

Ile His His Ala Leu Thr Val Glu Gly Gly Gly His Tyr Ala Cys Asp
                165                 170                 175

Ile Lys Thr Val Tyr Arg Ala Lys Lys Ala Ala Leu Lys Met Pro Gly
                180                 185                 190

Tyr His Tyr Val Asp Thr Lys Leu Val Ile Trp Asn Asn Asp Lys Glu
            195                 200                 205

Phe Met Lys Val Glu Glu His Glu Ile Ala Val Ala Arg His His Pro
        210                 215                 220

Phe Tyr Glu Pro Lys Lys Asp Lys
225                 230

<210> SEQ ID NO 11
<211> LENGTH: 229
<212> TYPE: PRT
<213> ORGANISM: Anemonia majano
<220> FEATURE:
<223> OTHER INFORMATION: Complete protein sequence of amFP486 (Figure 3)
<300> PUBLICATION INFORMATION:
<301> AUTHORS: Matz,M.V., Fradkov,A.F., Labas,Y.A., Savitsky,A.P.,
      Zaraisky,A.G., Markelov,M.L. and Lukyanov,S.A.
<302> TITLE: Fluorescent proteins from nonbioluminescent Anthozoa
      species
<303> JOURNAL: Nat. Biotechnol.
<304> VOLUME: 17
<305> ISSUE: 10
<306> PAGES: 969-973
<307> DATE: 1999
<308> DATABASE ACCESSION NUMBER: Q9U6Y6
<309> DATABASE ENTRY DATE: 2004-12-21
<313> RELEVANT RESIDUES IN SEQ ID NO: (1)..(229)

<400> SEQUENCE: 11

Met Ala Leu Ser Asn Lys Phe Ile Gly Asp Asp Met Lys Met Thr Tyr
 1               5                  10                  15

His Met Asp Gly Cys Val Asn Gly His Tyr Phe Thr Val Lys Gly Glu
                20                  25                  30

Gly Asn Gly Lys Pro Tyr Glu Gly Thr Gln Thr Ser Thr Phe Lys Val
            35                  40                  45

Thr Met Ala Asn Gly Gly Pro Leu Ala Phe Ser Phe Asp Ile Leu Ser
        50                  55                  60

Thr Val Phe Lys Tyr Gly Asn Arg Cys Phe Thr Ala Tyr Pro Thr Ser
 65                  70                  75                  80

Met Pro Asp Tyr Phe Lys Gln Ala Phe Pro Asp Gly Met Ser Tyr Glu
                85                  90                  95

Arg Thr Phe Thr Tyr Glu Asp Gly Gly Val Ala Thr Ala Ser Trp Glu
                100                 105                 110
```

```
Ile Ser Leu Lys Gly Asn Cys Phe Glu His Lys Ser Thr Phe His Gly
        115                 120                 125

Val Asn Phe Pro Ala Asp Gly Pro Val Met Ala Lys Lys Thr Thr Gly
    130                 135                 140

Trp Asp Pro Ser Phe Glu Lys Met Thr Val Cys Asp Gly Ile Leu Lys
145                 150                 155                 160

Gly Asp Val Thr Ala Phe Leu Met Leu Gln Gly Gly Asn Tyr Arg
                165                 170                 175

Cys Gln Phe His Thr Ser Tyr Lys Thr Lys Lys Pro Val Thr Met Pro
                180                 185                 190

Pro Asn His Val Val Glu His Arg Ile Ala Arg Thr Asp Leu Asp Lys
            195                 200                 205

Gly Gly Asn Ser Val Gln Leu Thr Glu His Ala Val Ala His Ile Thr
        210                 215                 220

Ser Val Val Pro Phe
225

<210> SEQ ID NO 12
<211> LENGTH: 236
<212> TYPE: PRT
<213> ORGANISM: Artificial
<220> FEATURE:
<223> OTHER INFORMATION: Complete protein sequence of mCherry (Figure 3)
<300> PUBLICATION INFORMATION:
<301> AUTHORS: Shaner,N.C., Campbell,R.E., Steinbach,P.A.,
       Giepmans,B.N., Palmer,A.E. and Tsien,R.Y.
<302> TITLE: Improved monomeric red, orange and yellow fluorescent
       proteins
<303> JOURNAL: Nat. Biotechnol.
<304> VOLUME: 22
<305> ISSUE: 12
<306> PAGES: 1567-1572
<307> DATE: 2004
<308> DATABASE ACCESSION NUMBER: AAV52164
<309> DATABASE ENTRY DATE: 2004-12-17
<313> RELEVANT RESIDUES IN SEQ ID NO: (1)..(236)

<400> SEQUENCE: 12

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
            20                  25                  30

Glu Ile Glu Gly Glu Gly Glu Gly Arg Pro Tyr Glu Gly Thr Gln Thr
        35                  40                  45

Ala Lys Leu Lys Val Thr Lys Gly Gly Pro Leu Pro Phe Ala Trp Asp
    50                  55                  60

Ile Leu Ser Pro Gln Phe Met Tyr Gly Ser Lys Ala Tyr Val Lys His
65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
    130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175
```

His Tyr Asp Ala Glu Val Lys Thr Thr Tyr Lys Ala Lys Lys Pro Val
            180                 185                 190

Gln Leu Pro Gly Ala Tyr Asn Val Asn Ile Lys Leu Asp Ile Thr Ser
        195                 200                 205

His Asn Glu Asp Tyr Thr Ile Val Glu Gln Tyr Glu Arg Ala Glu Gly
    210                 215                 220

Arg His Ser Thr Gly Gly Met Asp Glu Leu Tyr Lys
225                 230                 235

<210> SEQ ID NO 13
<211> LENGTH: 239
<212> TYPE: PRT
<213> ORGANISM: Artificial
<220> FEATURE:
<223> OTHER INFORMATION: Complete protein sequence of EGFP (Figure 3)

<400> SEQUENCE: 13

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
            85                  90                  95

Arg Thr Ile Phe Phe Lys Asp Asp Gly Asn Tyr Lys Thr Arg Ala Glu
        100                 105                 110

Val Lys Phe Glu Gly Asp Thr Leu Val Asn Arg Ile Glu Leu Lys Gly
    115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
            165                 170                 175

Val Gln Leu Ala Asp His Tyr Gln Gln Asn Thr Pro Ile Gly Asp Gly
        180                 185                 190

Pro Val Leu Leu Pro Asp Asn His Tyr Leu Ser Thr Gln Ser Ala Leu
    195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys
225                 230                 235

<210> SEQ ID NO 14
<211> LENGTH: 225
<212> TYPE: PRT
<213> ORGANISM: Artificial
<220> FEATURE:
<223> OTHER INFORMATION: Complete protein sequence of dsFP583 (Figure
      15)

<400> SEQUENCE: 14

```
Met Arg Ser Ser Lys Asn Val Ile Lys Glu Phe Met Arg Phe Lys Val
1               5                   10                  15

Arg Met Glu Gly Thr Val Asn Gly His Glu Phe Glu Ile Glu Gly Glu
                20                  25                  30

Gly Glu Gly Arg Pro Tyr Glu Gly His Asn Thr Val Lys Leu Lys Val
            35                  40                  45

Thr Lys Gly Gly Pro Leu Pro Phe Ala Trp Asp Ile Leu Ser Pro Gln
        50                  55                  60

Phe Gln Tyr Gly Ser Lys Val Tyr Val Lys His Pro Ala Asp Ile Pro
65              70                  75                  80

Asp Tyr Lys Lys Leu Ser Phe Pro Glu Gly Phe Lys Trp Glu Arg Val
                85                  90                  95

Met Asn Phe Glu Asp Gly Gly Val Val Thr Val Thr Gln Asp Ser Ser
            100                 105                 110

Leu Gln Asp Gly Cys Phe Ile Tyr Lys Val Lys Phe Ile Gly Val Asn
        115                 120                 125

Phe Pro Ser Asp Gly Pro Val Met Gln Lys Lys Thr Met Gly Trp Glu
130                 135                 140

Ala Ser Thr Glu Arg Leu Tyr Pro Arg Asp Gly Val Leu Lys Gly Glu
145                 150                 155                 160

Ile His Lys Ala Leu Lys Leu Lys Asp Gly Gly His Tyr Leu Val Glu
                165                 170                 175

Phe Lys Ser Ile Tyr Met Ala Lys Lys Pro Val Gln Leu Pro Gly Tyr
            180                 185                 190

Tyr Tyr Val Asp Ser Lys Leu Asp Ile Thr Ser His Asn Glu Asp Tyr
        195                 200                 205

Thr Ile Val Glu Gln Tyr Glu Arg Thr Glu Gly Arg His His Leu Phe
    210                 215                 220

Leu
225

<210> SEQ ID NO 15
<211> LENGTH: 225
<212> TYPE: PRT
<213> ORGANISM: Artificial
<220> FEATURE:
<223> OTHER INFORMATION: Complete protein sequence of mRFP1 (Figure 15)

<400> SEQUENCE: 15

Met Ala Ser Ser Glu Asp Val Ile Lys Glu Phe Met Arg Phe Lys Val
1               5                   10                  15

Arg Met Glu Gly Ser Val Asn Gly His Glu Phe Glu Ile Glu Gly Glu
                20                  25                  30

Gly Glu Gly Arg Pro Tyr Glu Gly Thr Gln Thr Ala Lys Leu Lys Val
            35                  40                  45

Thr Lys Gly Gly Pro Leu Pro Phe Ala Trp Asp Ile Leu Ser Pro Gln
        50                  55                  60

Phe Gln Tyr Gly Ser Lys Ala Tyr Val Lys His Pro Ala Asp Ile Pro
65              70                  75                  80

Asp Tyr Leu Lys Leu Ser Phe Pro Glu Gly Phe Lys Trp Glu Arg Val
                85                  90                  95

Met Asn Phe Glu Asp Gly Gly Val Val Thr Val Thr Gln Asp Ser Ser
            100                 105                 110

Leu Gln Asp Gly Glu Phe Ile Tyr Lys Val Lys Leu Arg Gly Thr Asn
        115                 120                 125
```

```
Phe Pro Ser Asp Gly Pro Val Met Gln Lys Lys Thr Met Gly Trp Glu
    130                 135                 140

Ala Ser Thr Glu Arg Met Tyr Pro Glu Asp Gly Ala Leu Lys Gly Glu
145                 150                 155                 160

Ile Lys Met Arg Leu Lys Leu Lys Asp Gly Gly His Tyr Asp Ala Glu
                165                 170                 175

Val Lys Thr Thr Tyr Met Ala Lys Lys Pro Val Gln Leu Pro Gly Ala
            180                 185                 190

Tyr Lys Thr Asp Ile Lys Leu Asp Ile Thr Ser His Asn Glu Asp Tyr
        195                 200                 205

Thr Ile Val Glu Gln Tyr Glu Arg Ala Glu Gly Arg His Ser Thr Gly
    210                 215                 220

Ala
225

<210> SEQ ID NO 16
<211> LENGTH: 235
<212> TYPE: PRT
<213> ORGANISM: Artificial
<220> FEATURE:
<223> OTHER INFORMATION: Complete protein sequence of avGFP (Figure 15)

<400> SEQUENCE: 16

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Val Gln Cys Phe Ser Arg Tyr Pro Asp His Met Lys Gln His Asp Phe
65                  70                  75                  80

Phe Lys Ser Ala Met Pro Glu Gly Tyr Val Gln Glu Arg Thr Ile Phe
                85                  90                  95

Phe Lys Asp Asp Gly Asn Tyr Lys Thr Arg Ala Glu Val Lys Phe Glu
            100                 105                 110

Gly Asp Thr Leu Val Asn Arg Ile Glu Leu Lys Gly Ile Asp Phe Lys
        115                 120                 125

Glu Asp Gly Asn Ile Leu Gly His Lys Leu Glu Tyr Asn Tyr Asn Ser
    130                 135                 140

His Asn Val Tyr Ile Met Ala Asp Lys Gln Lys Asn Gly Ile Lys Val
145                 150                 155                 160

Asn Phe Lys Ile Arg His Asn Ile Glu Asp Gly Ser Val Gln Leu Ala
                165                 170                 175

Asp His Tyr Gln Gln Asn Thr Pro Ile Gly Asp Gly Pro Val Leu Leu
            180                 185                 190

Pro Asp Asn His Tyr Leu Ser Thr Gln Ser Ala Leu Ser Lys Asp Pro
        195                 200                 205

Asn Glu Lys Arg Asp His Met Val Leu Leu Glu Phe Val Thr Ala Ala
    210                 215                 220

Gly Ile Thr His Gly Met Asp Glu Leu Tyr Lys
225                 230                 235

<210> SEQ ID NO 17
<211> LENGTH: 13
```

```
<212> TYPE: DNA
<213> ORGANISM: Artificial
<220> FEATURE:
<223> OTHER INFORMATION: Kozak sequence
<220> FEATURE:
<221> NAME/KEY: misc_feature
<222> LOCATION: (10)..(12)
<223> OTHER INFORMATION: "ATG" is the start codon

<400> SEQUENCE: 17
gccaccgcca tgc                                                          13

<210> SEQ ID NO 18
<211> LENGTH: 18
<212> TYPE: PRT
<213> ORGANISM: Artificial
<220> FEATURE:
<223> OTHER INFORMATION: endoplasmic reticulum targeting sequence of
      calreticulin

<400> SEQUENCE: 18

Met Leu Leu Ser Val Pro Leu Leu Leu Gly Leu Leu Gly Leu Ala Ala
1               5                   10                  15

Ala Asp

<210> SEQ ID NO 19
<211> LENGTH: 7
<212> TYPE: PRT
<213> ORGANISM: Artificial
<220> FEATURE:
<223> OTHER INFORMATION: sequence at N-terminus of synthetic variant
      dTFP0.10

<400> SEQUENCE: 19

Met Val Ser Lys Gly Glu Glu
1               5

<210> SEQ ID NO 20
<211> LENGTH: 7
<212> TYPE: PRT
<213> ORGANISM: Artificial
<220> FEATURE:
<223> OTHER INFORMATION: sequence at C-terminus of synthetic variant
      dTFP0.10

<400> SEQUENCE: 20

Gly Met Asp Glu Leu Tyr Lys
1               5

<210> SEQ ID NO 21
<211> LENGTH: 12
<212> TYPE: PRT
<213> ORGANISM: Artificial
<220> FEATURE:
<223> OTHER INFORMATION: linker sequence used to form synthetic variant
      tdTFP0.30

<400> SEQUENCE: 21

Thr Gly Ser Thr Leu Val Ser Gly Ser Gly Thr Ala
1               5                   10

<210> SEQ ID NO 22
<211> LENGTH: 6
<212> TYPE: PRT
<213> ORGANISM: Artificial
<220> FEATURE:
<223> OTHER INFORMATION: sequence from residues L223 to A228 used to
      form synthetic variant mTFP0.6
```

```
<400> SEQUENCE: 22

Leu Leu Pro Ser Gln Ala
1               5
```